US012799501B2

(12) United States Patent
Qu et al.

(10) Patent No.: US 12,799,501 B2
(45) Date of Patent: Nov. 17, 2026

(54) PLASMID FREE AAV VECTOR PRODUCING CELL LINES

(71) Applicant: Spark Therapeutics, Inc., Philadelphia, PA (US)

(72) Inventors: Guang Qu, Sicklerville, NJ (US); Denis Phichith, West Chester, PA (US); Jingmin Zhou, Wallingford, PA (US)

(73) Assignee: Spark Therapeutics, Inc., Philadelphia, PA (US)

( * ) Notice: Subject to any disclaimer, the term of this patent is extended or adjusted under 35 U.S.C. 154(b) by 1347 days.

(21) Appl. No.: 17/052,097

(22) PCT Filed: May 7, 2019

(86) PCT No.: PCT/US2019/031209
§ 371 (c)(1),
(2) Date: Oct. 30, 2020

(87) PCT Pub. No.: WO2019/217483
PCT Pub. Date: Nov. 14, 2019

(65) Prior Publication Data

US 2022/0025396 A1 Jan. 27, 2022

Related U.S. Application Data

(60) Provisional application No. 62/668,119, filed on May 7, 2018.

(51) Int. Cl.
*C12N 7/04* (2006.01)
*C12N 15/86* (2006.01)

(52) U.S. Cl.
CPC .... *C12N 15/86* (2013.01); *C12N 2750/14122* (2013.01); *C12N 2750/14123* (2013.01);
(Continued)

(58) Field of Classification Search
None
See application file for complete search history.

(56) References Cited

U.S. PATENT DOCUMENTS 5,872,005 A 2/1999 Wang et al.
6,953,690 B1 10/2005 Gao
(Continued)

FOREIGN PATENT DOCUMENTS

JP 2002-506652 A 3/2002
JP 2005-522994 A 8/2005
(Continued)

OTHER PUBLICATIONS

Ayuso, E, et al., Production, Purification and Characterization of Adeno-Associated Vectors, Current Gene4Therapy, 2010, 10(6):1-15.

(Continued)

*Primary Examiner* — M Franco G Salvoza
(74) *Attorney, Agent, or Firm* — Baker Botts L.L.P.

(57) ABSTRACT

Disclosed herein are packaging cell lines, in which adenovirus (Ad) E1A is constitutively expressed, that also contain integrated AAV rep and cap genes. The packaging cell lines exhibit little to no expressed Rep protein until helper virus function, such as adenovirus (Ad) E4, E2A and/or VA RNA are provided by, for example, transduction of the cells with a virus, vector or plasmid, such as an Ad-AAV hybrid virus. The promoter driving expression of AAV rep gene can be positioned far enough upstream (5') of the rep coding sequence that E1A is unable to activate the promoter, activate substantial transcription of the rep gene and in turn produce Rep protein. Introduction of helper virus function, such as E2A, E4 and/or VA RNA into these packaging cells
(Continued)

is able to drive AAV rep gene transcription, subsequent Rep protein expression and production of rAAV vector particles.

29 Claims, 5 Drawing Sheets

Specification includes a Sequence Listing.

(52) U.S. Cl.
CPC .............. *C12N 2750/14143* (2013.01); *C12N 2750/14152* (2013.01)

(56) References Cited

U.S. PATENT DOCUMENTS

| | | | |
|---|---|---|---|
| 9,441,206 | B2 | 9/2016 | Grieger et al. |
| 2003/0040101 | A1 | 2/2003 | Wilson et al. |
| 2005/0148076 | A1 | 7/2005 | Allen |
| 2014/0087444 | A1 | 3/2014 | Bennett et al. |

FOREIGN PATENT DOCUMENTS

| | | | | |
|---|---|---|---|---|
| WO | WO-9941399 | A1 * | 8/1999 | ........... C07K 14/705 |
| WO | 1999047691 | A1 | 9/1999 | |
| WO | 2003052052 | A2 | 6/2003 | |
| WO | WO-2017096039 | A1 * | 6/2017 | ............. C12N 15/85 |

OTHER PUBLICATIONS

Emmerling, V.V, et al., Novel approaches to render stable producer cell lines viable for the commercial manufacturing of rAAV-based gene therapy vectors, BMC Proceedings 2013, 7(Suppl 6):P12.
Martin, J., et al., Generation and Characterization of Adeno-Associated Virus Producer Cell Lines for Research and Preclinical Vector Production, Human Gene Therapy Methods, Aug. 2013, 24:253-269.
Nakamura, S., et al., Development of packaging cell lines for generation of adeno-associated virus vectors by lentiviral gene transfer of trans-complementary components, Eur. J. Haematol, 2004, 73:285-294.
Qiao, C., et al., Feasibility of Generating Adeno-Associated Virus Packaging Cell Lines Containing Inducible Adenovirus Helper Genes, Journal of Virology, Feb. 2002, 76(4):1904-1913.
Qiao, C., et al., A Novel Gene Expression Control System and Its Use in Stable, High-Titer 293 Cell-Based Adeno-Associated Virus Packaging Cell Lines, Journal of Virology, Dec. 2002, 76(24):13015-13027.
Yuan, Z., et al., A Versatile Adeno-Associated Virus Vector Producer Cell Line Method for Scalable Vector Production of Different Serotypes, Human Gene Therapy, May 2011, 22:613-624.
Mizukami, H., et al., Separate Control of Rep and Cap Expression Using Mutant and Wild-Type LoxP Sequences and Improved Packaging System for Adeno-Associated Virus Vector Production, Molecular Biology, May 1, 2004, pp. 7-14, vol. 27, No. 1.

* cited by examiner

AAV Production (vg/ml)

Day 5
qPCR

| m.o.i | 0.16 | 0.8 | 1.6 | 3.2 |
|---|---|---|---|---|
| LK03 | 7.05 E+9 | 2.1 E+9 | 7.4 E+8 | 2.4 E+10 |

Positive control, triple transfection: 2.1 E+10

AAV Production (vg/ml)

Day 3
qPCR

| m.o.i | 0.16 | 0.8 | 1.6 | 3.2 |
|---|---|---|---|---|
| LK03 | 1.8 E+9 | 4.5 E+9 | 8.9 E+8 | 2.2 E+10 |

<u>Positive control, triple transfection</u>: 3.2 E+10

SEQUENCE LISTING

<160> NUMBER OF SEQ ID NOS: 4

<210> SEQ ID NO 1
<211> LENGTH: 1749
<212> TYPE: DNA
<213> ORGANISM: Artificial Sequence
<220> FEATURE:
<223> OTHER INFORMATION: Cloning vector

<400> SEQUENCE: 1
gcgcagccgc caagccgaat tctgcagata tccatcacac tggcggccgc tcgactagag 60
cggccgccac cgcggtggag ctccagcttt tgttcccttt agtgagggtt aattgcgcgc 120
ttggcgtaat catggtcata gctgtttcct gtgtgaaatt gttatccgct cacaattcca 180
cacaacatac gagccggaag cataaagtgt aaagcctggg gtgcctaatg agtgagctaa 240
ctcacattaa ttgcgttgcg ctcactgccc gctttccagt cgggaaacct gtcgtgccag 300
ctgcattaat gaatcggcca acgcgcgggg agaggcggtt tgcgtattgg gcgctcttcc 360
gcttcctcgc tcactgactc gctgcgctcg gtcgttcggc tgcggcgagc ggtatcagct 420
cactcaaagg cggtaatacg gttatccaca gaatcagggg ataacgcagg aaagaacatg 480
tgagcaaaag gccagcaaaa ggccaggaac cgtaaaaagg ctttctacgg ggtctgacgc 540
tcagtggaac tccgtcgaga ggtctgcctc gtgaagaagg tgttgctgac tcataccagg 600
cctgaatcgc cccatcatcc agccagaaag tgagggagcc acggttgatg agagctttgt 660
tgtaggtgga ccagttggtg attttgaact tttgctttgc cacggaacgg tctgcgttgt 720
cgggaagatg cgtgatctga tccttcaact cagcaaaagt tcgatttatt caacaaagcc 780
acgttgtgtc tcaaaatctc tgatgttaca ttgcacaaga taaaaatata tcatcatgaa 840
caataaaact gtctgcttac ataaacagta atacaagggg tgtttaatca gaattggtta 900
attggttgta acactggcag agcattacgc tgacttgacg ggacggcggc tttgttgaat 960
aaatcgcatt cgccattcag gctgcgcaac tgttgggaag ggcgatcggt gcgggcctct 1020
tcgctattac gccagctggc gaaaggggga tgtgctgcaa ggcgattaag ttgggtaacg 1080
ccagggtttt cccagtcacg acgttgtaaa acgacggcca gtgccaagct tgcatgcctg 1140
caggtctaaa tcaaaagaat agcccgagat agagttgagt gttgttccag tttggaacaa 1200
gacgaaaaac cgtctatcag ggcgatggcc cactacgtga accatcaccc taatcaagtt 1260
ttttggggtc gaggtgccgt aaagcactaa atcggaaccc taaagggagc ccccgattta 1320
gagcttgacg gggaaagccg gcgaacgtgg cgagaaagga agggaagaaa gcgaaaggag 1380
cgggcgctag ggcgctggca agtgtagcgg tcacgctgcg cgtaaccacc acacccgccg 1440
cgcttaatgc gccgctacag ggcgcgtccc attcgccatt caggctgcgc aactgttggg 1500
aagggcgatc ggtgcgggcc tcttcgctat tacgccagct ggcgaaaggg ggatgtgctg 1560
caaggcgatt aagttgggta acgccagggt tttcccagtc acgacgttgt aaaacgacgg 1620
ccagtgagcg cgcgtaatac gactcactat agggcgaatt gggtaccggg ccccccctcg 1680
aggtcgacgg tatcggggga gctcgcaggg tctccatttt gaagcgggag gtttgaacgc 1740
gcagccgcc 1749

<210> SEQ ID NO 2
<211> LENGTH: 162
<212> TYPE: DNA
<213> ORGANISM: Adeno-associated virus

<400> SEQUENCE: 2
gaggggtgga gtcgtgacgt gaattacgtc atagggttag ggaggtcctg tattagaggt 60
cacgtgagtg ttttgcgaca ttttgcgaca ccatgtggtc acgctgggta tttaagcccg 120
agtgagcacg cagggtctcc attttgaagc gggaggtttg aa 162

<210> SEQ ID NO 3
<211> LENGTH: 736
<212> TYPE: PRT
<213> ORGANISM: Artificial Sequence
<220> FEATURE:
<223> OTHER INFORMATION: Adeno-associated virus capsid protein

<400> SEQUENCE: 3

Met Ala Ala Asp Gly Tyr Leu Pro Asp Trp Leu Glu Asp Asn Leu Ser
1 5 10 15

Glu Gly Ile Arg Glu Trp Trp Ala Leu Gln Pro Gly Ala Pro Lys Pro
20 25 30

Lys Ala Asn Gln Gln His Gln Asp Asn Ala Arg Gly Leu Val Leu Pro
35 40 45

Gly Tyr Lys Tyr Leu Gly Pro Gly Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Lys Tyr Asn His Ala
85 90 95

Asp Ala Glu Phe Gln Glu Arg Leu Lys Glu Asp Thr Ser Phe Gly Gly
100 105 110

Asn Leu Gly Arg Ala Val Phe Gln Ala Lys Lys Arg Leu Leu Glu Pro
115 120 125

Leu Gly Leu Val Glu Glu Ala Ala Lys Thr Ala Pro Gly Lys Lys Arg
130 135 140

Pro Val Asp Gln Ser Pro Gln Glu Pro Asp Ser Ser Ser Gly Val Gly
145 150 155 160

Lys Ser Gly Lys Gln Pro Ala Arg Lys Arg Leu Asn Phe Gly Gln Thr
165 170 175

Gly Asp Ser Glu Ser Val Pro Asp Pro Gln Pro Leu Gly Glu Pro Pro
180 185 190

Ala Ala Pro Thr Ser Leu Gly Ser Asn Thr Met Ala Ser Gly Gly Gly
195 200 205

Ala Pro Met Ala Asp Asn Asn Glu Gly Ala Asp Gly Val Gly Asn Ser
210 215 220

Ser Gly Asn Trp His Cys Asp Ser Gln Trp Leu Gly Asp Arg Val Ile
225 230 235 240

Thr Thr Ser Thr Arg Thr Trp Ala Leu Pro Thr Tyr Asn Asn His Leu
245 250 255

Tyr Lys Gln Ile Ser Ser Gln Ser Gly Ala Ser Asn Asp Asn His Tyr
260 265 270

Phe Gly Tyr Ser Thr Pro Trp Gly Tyr Phe Asp Phe Asn Arg Phe His
275 280 285

Cys His Phe Ser Pro Arg Asp Trp Gln Arg Leu Ile Asn Asn Asn Trp
290 295 300

Gly Phe Arg Pro Lys Lys Leu Ser Phe Lys Leu Phe Asn Ile Gln Val
305 310 315 320

Lys Glu Val Thr Gln Asn Asp Gly Thr Thr Thr Ile Ala Asn Asn Leu
325 330 335

-continued

```
Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Pro Leu
                725                 730                 735
```

<210> SEQ ID NO 4
<211> LENGTH: 738

-continued

<212> TYPE: PRT
<213> ORGANISM: Artificial Sequence
<220> FEATURE:
<223> OTHER INFORMATION: Adeno-associated virus capsid protein

<400> SEQUENCE: 4

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Ser Pro Val Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380
```

-continued

```
Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Asn Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu
```

PLASMID FREE AAV VECTOR PRODUCING CELL LINES

RELATED APPLICATIONS

This patent application is the National Phase of International Application No. PCT/US2019/031209, filed May 7, 2019, which designated the U.S. and that International Application was published under PCT Article 21(2) in English, which claims the benefit of priority to U.S. Provisional Patent Application No. 62/668,119, filed May 7, 2018. The entire content of the foregoing applications is incorporated herein by reference, including all text, tables, sequence listing and drawings.

SEQUENCE LISTING

The instant application contains a Sequence Listing which has been submitted electronically in ASCII format and is hereby incorporated by reference in its entirety. Said ASCII copy, created on Oct. 30, 2020, is named "Spark0515849_ST25.txt" and is 15.5 KB in size.

INTRODUCTION

There are currently several rAAV production systems used to produce rAAV vectors, such as plasmid transient transfection of human embryonic kidney (HEK) 293 cells, Hela producer cell line, BHK21 platform, and baculovirus-based production systems. Each of these methods has its strengths and weaknesses.

Certain features of Ela-expressing cells, such as HEK293 cells, render them attractive for the production of rAAV, including ease of growth and adaptability to growth in suspension. Efforts to create stable and passagable AAV packaging cell lines in cells such as HEK293 cells have been hampered by cellular toxicity caused by the AAV Rep protein, which is activated by E1A.

The invention disclosed herein successfully introduced Rep/Cap genes into a human cell line, HEK293F. The rAAV particle yield provided by this cell system can be greater than the yield obtained with the current triple-plasmid transfection method. Furthermore, the cells produce rAAV vector particles in which potential contamination by transfection reagents or rDNA is reduced, the cost required for the rDNA necessary in transient transfection methods is reduced, and the cells provide a platform are AAV vector particle production process that is more robust than the triple transfection method, and is scalable and transferable to any AAV serotype.

SUMMARY

Disclosed herein is a stable packaging cell line, in which adenovirus (Ad) E1 is constitutively expressed, that also contains integrated AAV rep and cap genes, but has little to no expression of Rep protein until helper virus function, such as adenovirus (Ad) E4, E2A and/or VA RNA are provided by transduction of the cells with a vector or virus, such as an Ad-AAV hybrid virus. In one embodiment, the promoter driving expression of AAV rep is positioned far enough upstream of the rep coding sequence that E1 is unable to activate the promoter, activate substantial transcription of rep and in turn substantial translation of Rep protein. Introduction of helper virus function, such as E2A, E4 and/or VA into these cells is able to drive or stimulate AAV rep gene transcription and subsequent Rep protein expression.

In accordance with the invention, mammalian cell lines are provided that adenovirus (Ad) E1A protein in which an adeno-associated virus (AAV) rep gene operably linked to a promoter has been integrated, and in which a nucleic acid spacer is positioned between the rep gene and the promoter, and in which an AAV cap gene has also been integrated.

In various embodiments, a cell line of the invention is passagable for at least about 5 passages, at least about 10 passages, at least about 15 passages, or at least about 20 passages while E1A protein is expressed in the cell line.

In various embodiments, a cell line of the invention is passagable for at least about 5 passages, at least about 10 passages, at least about 15 passages, or at least about 20 passages without substantial death of the cell line.

In various embodiments, in a cell line of the invention Rep protein is expressed from the rep gene at levels that do not cause substantial death of the cell line when cultured in growth media.

In various embodiments, in a cell line of the invention Rep protein expression from the rep gene increases in the presence of helper virus function.

In various embodiments, in a cell line of the invention the promoter drives expression of the rep gene only in the presence of helper virus function.

Adenovirus 5 (Ad5) of each of E4, E2A and VA are exemplified helper virus function, but other Ad types and/or other helper virus functions are compatible. For example, other viruses such as adenovirus, herpesvirus pox viruses and hybrid viruses can be used. For example, an Ad-AAV hybrid virus may be used to provide helper virus function and which, also optionally, provides a transgene of interest, flanked by ITRs.

In various embodiments, the helper virus function comprises or is provided by one or more viruses, vectors or plasmids that provide the helper virus function.

In various embodiments, the helper virus function comprises at least one of adenovirus (Ad) E2A protein, Ad E4 protein and Ad VA RNA.

In particular aspects, the at least one of Ad E2A, Ad E4 and Ad VA RNA are expressed by transcription from a polynucleotide sequence encoding the at least one of Ad E2A, Ad E4 and Ad VA RNA.

In various aspects, the polynucleotide sequence encoding the at least one of Ad E2A, Ad E4 and Ad VA RNA comprises one or more vectors.

In various aspects, the polynucleotide sequence encoding the at least one of Ad E2A, Ad E4 and Ad VA RNA comprises one or more plasmids.

In various aspects, the helper virus function is provided by one or more viruses, viral vectors, or plasmids.

In various aspects, the helper virus function is provided by a hybrid Ad-AAV virus comprising at least one of Ad E2A protein, Ad E4 protein and Ad VA RNA.

In various aspects, the hybrid Ad-AAV virus further comprises a heterologous nucleic acid sequence, optionally flanked at the 5' and/or 3' end by AAV inverted terminal repeats (ITRs).

In various embodiments, the parental clones selected to generate rAAV producing cell lines are engineered from HEK293F cells (HEK293 cells adapted to serum-free, suspension culture) by inserting AAV rep/cap genes using lentivirus as a shuttle vector. The human cell lines of the invention are viable over multiple passages due to low or undetectable AAV Rep protein, even in the presence of the Ad E1 gene and expression of the Ela protein.

In one embodiment, rAAV particle production from these cell lines is triggered by a single transduction by an Ad-AAV hybrid virus (for example, a hybrid virus comprised of adenovirus 5 having a deletion of the E1/E3 genes and AAV sequences, such as AAV ITRs flanking a transgene of interest). Once the cells of the invention are transduced (or infected) with, for example, the Ad-AAV hybrid virus, they effectively become "producer" cells, producing rAAV vector particles and eventually dying out in the process.

In one embodiment, little or no expression of Rep protein is achieved by attenuation of a constitutive promoter, such as AAV p5 promoter. Attenuation of promoter activity avoids or minimizes cell toxicity caused by the expressed AAV Rep protein.

In certain embodiments, the promoter operably linked or driving expression of AAV rep in the packaging cells of the invention is positioned, via a nucleic acid spacer, far enough upstream of the rep coding sequence that E1A is unable to activate the promoter and unable to drive substantial transcription of rep, and in turn substantial translation of Rep protein.

In one embodiment, the packaging cell has Rep in the HEK293 background, and in spite of the presence of constitutive expression of adenovirus E1A, substantial Rep toxicity is avoided.

In one embodiment, the p5 promoter is positioned far enough upstream (5') of the rep coding sequence that Ela is unable to activate the p5 promoter and drive substantial transcription of rep. Introduction of adenovirus E2A, E4 and VA RNA via the Ad-AAV hybrid virus or other viruses, vectors and/or plasmids into these cells is able to drive rep gene expression and subsequent translation of Rep protein.

In various embodiments, the promoter is a constitutively active promoter.

In various embodiments, the promoter is a non-inducible promoter.

In various embodiments, the promoter comprises a polynucleotide sequence having at least 90% identity to the sequence of SEQ ID NO:2.

In various embodiments, the promoter comprises a polynucleotide sequence having at least 90% identity to an AAV1 p5 promoter, AAV3 p5 promoter, AAV4 p5 promoter, AAV5 p5 promoter, AAV6 p5 promoter, AAV7 p5 promoter, AAV8 p5 promoter, AAV9 p5 promoter, AAV10 p5 promoter, or AAV11 p5 promoter.

In various embodiments, the rep gene encodes an AAV1 Rep protein, an AAV2 Rep protein, an AAV3 Rep protein, an AAV4 Rep protein, an AAV5 Rep protein, an AAV6 Rep protein, an AAV7 Rep protein, an AAV8 Rep protein, an AAV9 Rep protein, an AAV10 Rep protein, or an AAV11 Rep protein.

In various embodiments, the cap gene is operably linked to a promoter.

In certain embodiments, the rep gene and the cap gene are integrated in tandem into chromosomal nucleic acid of the cell line.

In certain embodiments, AAV rep and cap genes are arranged essentially as in the native AAV genome, except that there is a spacer between the rep gene and the operably linked promoter. Such an exemplary arrangement is illustrated in FIG. 2, where rep and cap genes are arranged in a tandem configuration.

In certain embodiments, AAV rep and cap genes are not arranged essentially as in the native AAV genome. For example, rep and cap genes need not be arranged in a tandem configuration, and may be separated from each other.

In certain embodiments, Rep protein is expressed from the rep gene at levels at least 5-fold lower than in the absence of the nucleic acid spacer being positioned between the rep gene and the promoter, or at levels at least 10-fold lower than in the absence of the nucleic acid spacer being positioned between the rep gene and the promoter, or at levels at least 15-fold lower than in the absence of the nucleic acid spacer being positioned between the rep gene and the promoter, or at levels at least 20-fold lower than in the absence of the nucleic acid spacer being positioned between the rep gene and the promoter, or at levels at least 25-fold lower than in the absence of the nucleic acid spacer being positioned between the rep gene and the promoter, or at levels 25-100-fold lower than in the absence of the nucleic acid spacer being positioned between the rep gene and the promoter, or at levels 50-1,000 fold lower than in the absence of the nucleic acid spacer being positioned between the rep gene and the promoter.

In certain embodiments, a cell line of the invention further includes a heterologous nucleic acid sequence, wherein the heterologous nucleic acid sequence is optionally flanked at the 5' and/or 3' end by AAV inverted terminal repeats (ITRs).

In particular aspects the AAV ITRs comprise one or more ITRs of any of: AAV1, AAV2, AAV3, AAV4, AAV5, AAV6, AAV7, AAV8, AAV9, AAV10, AAV11, Rh10, Rh74 or AAV-3B AAV serotypes, or a combination thereof.

In certain embodiments, a cell line of the invention is a mammalian adeno-associated virus (AAV) packaging cell line, in which the cell line expresses adenovirus (Ad) E1A protein, the cell line comprises an integrated AAV rep gene operably linked to an AAV p5 promoter in which a nucleic acid spacer of from about 1700 to about 1800 nucleotides is positioned between the rep gene and the p5 promoter, and the selling comprises an integrated AAV cap gene, in which the Rep protein is expressed from rep rep gene only in the presence of helper virus function provided by Ad E2A protein, Ad E4 protein and Ad VA RNA.

In certain embodiments, invention cell clones are engineered from HEK293F cells by inserting AAV rep/cap genes, each of a desired/selected serotype, into the HEK293F cell genome using a lentivirus as a shuttle vector. It is advantageous to produce recombinant AAV viral particles in human cells, such as HEK293F cells, having human cellular processes, including human cellular posttranslational modifications, thereby improving the safety and bioactivity of the final products.

One appeal of this invention is that rAAV production from these clones can be triggered by a single transduction by, for example, recombinant hybrid virus of adenovirus 5 (with deleted E1/E3 genes) and AAV (hybrid Ad-AAV virus), which hybrid virus provides the helper functions (E2A, E4 and VA RNA from Ad5) and a gene of interest (heterologous nucleic acid) flanked by AAV ITRs to enable packaging of the recombinant AAV genome containing the heterologous nucleic acid sequence into rAAV particles.

Accordingly, also disclosed herein are AAV vector packaging systems. In one embodiment, an AAV vector packaging system includes a mammalian cell line as set forth herein and at least one virus, vector or plasmid comprising helper virus functions and optionally an AAV vector genome.

In various embodiments, in a packaging system of the invention at least one virus comprises an adenovirus-AAV hybrid that includes a polynucleotide sequence encoding Ad E2A protein, Ad E4 protein and Ad VA RNA; and a heterologous nucleic acid sequence, in which the heterologous nucleic acid sequence is optionally flanked at the 5' and/or 3' end by AAV inverted terminal repeats (ITRs).

In certain aspects, at least one virus comprises an adenovirus, herpesvirus, or poxvirus.

In certain embodiments, at least one vector comprises: a polynucleotide sequence encoding Ad E2A protein, Ad E4 protein and Ad VA RNA; and a heterologous nucleic acid sequence, the heterologous nucleic acid sequence optionally flanked at the 5' and/or 3' end by AAV inverted terminal repeats (ITRs), wherein the polynucleotide sequence of (a) and the heterologous nucleic acid sequence of (b) are in the same vector, or wherein the polynucleotide sequence of (a) and the heterologous nucleic acid sequence of (b) are in separate vectors.

In certain aspects, the least one vector comprises at least one viral vector.

In certain embodiments, the at least one plasmid comprises: a polynucleotide sequence encoding Ad E2A protein, Ad E4 protein and Ad VA RNA; and a heterologous nucleic acid sequence, the heterologous nucleic acid sequence is optionally flanked at the 5' and/or 3' end by AAV inverted terminal repeats (ITRs), wherein the polynucleotide sequence of (a) and the heterologous nucleic acid sequence of (b) are in the same plasmid, or in which the polynucleotide sequence of (a) and the heterologous nucleic acid sequence of (b) are in separate plasmids.

In certain embodiments, the AAV vector genome comprises a heterologous nucleic acid sequence, and the heterologous nucleic acid sequence is optionally flanked at the 5' and/or 3' end by AAV inverted terminal repeats (ITRs).

In certain embodiments, the heterologous nucleic acid sequence is flanked at the 5' and/or 3' end by AAV inverted terminal repeats (ITRs).

In certain embodiments, the AAV vector genome or the heterologous nucleic acid sequence comprises a virus, vector or plasmid.

In certain embodiments, the rep and/or cap genes were or are introduced into the cell line by way of a virus, vector or plasmid.

In certain aspects, the rep and/or cap genes were or are introduced into the cell line by way of a lentiviral vector.

In certain embodiments, the virus, vector or plasmid lacks genes encoding Ad E1A and/or E3 proteins.

In certain embodiments, the cell line is not a HeLa or A549 cell line.

In certain embodiments, the cell line comprises human embryonic kidney (HEK) cells.

In certain embodiments, the cell line comprises HEK293 cells or HEK293F cells.

In certain embodiments, the cell line does not express SV40 large T antigen.

In certain embodiments, the cell line is a suspension cell line or an adherent cell line.

In certain embodiments, the cell line can be cultured at a cell density of at least about $1\times10^6$, at least about $5\times10^6$, at least about $1\times10^7$ or at least about $2\times10^7$ cells/mL.

In certain embodiments, the cell line can be cultured at a cell density from about $1\times10^6$-$5\times10^6$, from about $5\times10^6$-$1\times10^7$, or from about $1\times10^7$-$2\times10^7$ cells/mL.

In certain embodiments, the expression of the AAV cap is driven by an AAV p40 promoter.

In certain embodiments, maintaining the E1A, rep and/or cap gene or protein expression in the cell line does not require expression of a selectable marker or selective pressure.

In certain aspects, the selectable marker comprises an antibiotic resistance gene and the selective pressure comprises a drug or an antibiotic.

In certain embodiments, the gene encoding the Ad E1A and/or the rep gene is not disrupted by an intron having transcription termination sequences flanked by lox P sites.

In certain embodiments, the expression of the rep gene is driven by an AAV p5 promoter positioned less than about 5,000 nucleotides 5' of the rep gene start codon.

In certain embodiments, the expression of the rep gene is driven by an AAV p5 promoter positioned about 25-5,000 nucleotides 5' of the rep gene start codon.

In certain embodiments, the expression of the rep gene is driven by an AAV p5 promoter positioned about 250-2,500 nucleotides 5' of the rep gene start codon.

In certain embodiments, the expression of the rep gene is driven by an AAV p5 promoter positioned about 500-2,000 nucleotides 5' of the rep gene start codon.

In certain embodiments, the expression of the rep gene is driven by an AAV p5 promoter positioned about 1,000-1,900 nucleotides 5' of the rep gene start codon.

In certain embodiments, the rep gene is driven by an AAV p5 promoter positioned at least about 1,500-1,900 nucleotides 5' of the rep gene start codon.

In certain embodiments, the expression of the rep gene is driven by an AAV p5 promoter positioned at least about 1,600-1,800 nucleotides 5' of the rep gene start codon.

In certain embodiments, the expression of the rep gene is driven by an AAV p5 promoter positioned at least about 1,700-1,800 nucleotides 5' of the rep gene start codon.

In certain embodiments, the expression of the rep gene is driven by an AAV p5 promoter in which there is a spacer sequence located between the 3' end of the AAV p5 promoter and the 5' end of the rep gene start codon, wherein the spacer sequence has a length of from about 250 to about 5,000 nucleotides.

The invention also provides cell lines and packaging systems in a culture or growth medium or a medium suitable for storage.

In certain embodiments, the cell line is in a medium suitable for long-term storage and preservation of cell viability.

In particular aspects, the cell line is in a medium suitable for long-term storage at or below 0°, at or below −30°, at or below −80° or at or below −160° C.

Also disclosed herein are methods of producing an invention cell line as set forth herein. In one embodiment, a method includes transfecting mammalian cells under conditions allowing introduction of the genes and expression of the genes and/or proteins as set forth herein. In particular aspects, a mammalian cell expresses Ad E1A and is transfected with rep and cap genes, in which the rep gene is operably linked to a promoter and in which a spacer sequence is positioned between the rep gene and the operably linked promoter. Transfected mammalian cells are selected for integrated rep and cap genes.

Further disclosed herein are methods of producing AAV particles. Such AAV particles include AAV vector particles as well as empty AAV particles.

In one embodiment, a method of producing rAAV vector particles includes transfecting a cell line as set forth herein with: (a) one or more virus, vector or plasmid, which virus vector or asthma comprises a rAAV vector genome comprising a heterologous nucleic acid sequence flanked at the 5' and/or 3' end by AAV ITRs; and (b) helper virus functions, thereby producing transfected cells with an AAV vector genome comprising a heterologous nucleic acid sequence and helper virus functions; and culturing the transfected cells under conditions allowing production of the rAAV vector particles.

In particular aspects, in a method of producing rAAV vector particles, the AAV vector genome of (a) and the helper virus functions of (b) are provided by a single virus, vector or plasmid.

In further particular aspects, in a method of producing rAAV vector particles, the AAV vector genome of (a) and the helper virus functions of (b) are provided by two or more viruses, vectors or plasmids.

In another embodiment, a method of producing rAAV vector particles includes transfecting an invention cell line that expresses E1A, has integrated rep and cap genes and comprises an AAV vector genome comprising a heterologous nucleic acid sequence flanked at 5' and/or 3' end by AAV ITRs with a virus, vector or plasmid comprising polynucleotides encoding Ad E2A, Ad E4 proteins and Ad VA RNA, thereby producing transfected cells, and culturing the transfected cells under conditions allowing production of the rAAV vector particles.

As set forth herein, AAV particles produced by cell lines and methods of the invention include empty AAV particles. Such empty AAV particles are devoid of a complete AAV vector genome and heterologous nucleic acid sequence. In one embodiment, empty AAV particles are produced by merely excluding an AAV vector genome and/or a heterologous nucleic acid sequence, and the cell line that expresses E1A and has integrated rep and cap genes when provided with helper virus function will assemble AAV particles that are devoid of a complete AAV vector genome and heterologous nucleic acid sequence. Such empty AAV particles are useful as decoys to absorb AAV neutralizing antibodies thereby allowing treatment of patients that have developed or are at risk of developing AAV neutralizing antibodies prior to, concomitant with, or after being administered a rAAV vector for gene therapy. Amounts of empty AAV particles produced may be comparable to amounts of rAAV vector particles having an AAV vector genome with a heterologous nucleic acid sequence.

Accordingly, the invention provides methods of producing empty AAV particles.

In one embodiment, a method of producing empty AAV particles includes: (a) transfecting invention cell line with one or more virus, vector or plasmid comprising helper virus functions, thereby producing transfected cells with helper virus functions; and (b) culturing the transfected cells under conditions allowing production of the empty AAV particles.

In certain embodiments of the methods of producing rAAV vector particles and empty AAV particles, the transfected cells produce rAAV vector particles at a yield of about $1\times10^{10}$ to about $5\times10^{12}$ vector genomes (vg)/mL or produce empty AAV particles at a yield of about $1\times10^{10}$ to about $5\times10^{12}$ particles/mL, the transfected cells produce AAV vector particles at a yield of about $5\times10^{10}$ to about $3\times10^{12}$ vector genomes (vg)/mL or produce empty AAV particles at a yield of about $5\times10^{10}$ to about $3\times10^{12}$ particles/mL, the transfected cells produce rAAV vector particles at a yield of about $1\times10^{11}$ to about $2\times10^{12}$ vector genomes (vg)/mL or produce empty AAV particles at a yield of about $1\times10^{11}$ to about $2\times10^{12}$ particles/mL.

In certain embodiments of the methods of producing rAAV vector particles and empty AAV particles, the method includes a step of collecting the cells and/or cell culture medium comprising the rAAV vector particles or the empty AAV particles.

In certain embodiments of the methods of producing rAAV vector particles and empty AAV particles, the method includes a step of collecting, isolating, or purifying the rAAV vector particles or the empty AAV particles.

Heterologous nucleic acid sequence(s) herein include without limitation nucleic acid sequences encoding a therapeutic protein(s) or an inhibitory nucleic acid sequence(s).

In one embodiment, a therapeutic protein(s) comprises a blood clotting factor or immunoglobulin sequence.

In one embodiment, the inhibitory nucleic acid sequence comprises a small or short hairpin (sh)RNA, microRNA (miRNA), small or short interfering (si)RNA, trans-splicing RNA, or antisense RNA.

In one embodiment, the heterologous nucleic acid sequence encodes a gene product selected from the group consisting of insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor α (TGFα), platelet-derived growth factor (PDGF), insulin growth factors I and II (IGF-I and IGF-II), TGFβ, activins, inhibins, bone morphogenic protein (BMP), nerve growth factor (NGF), brain-derived neurotrophic factor (BDNF), neurotrophins NT-3 and NT4/5, ciliary neurotrophic factor (CNTF), glial cell line derived neurotrophic factor (GDNF), neurturin, agrin, netrin-1 and netrin-2, hepatocyte growth factor (HGF), ephrins, noggin, sonic hedgehog and tyrosine hydroxylase.

In one embodiment, the heterologous nucleic acid sequence encodes a gene product selected from the group consisting of thrombopoietin (TPO), interleukins (I through IL-36), monocyte chemoattractant protein, leukemia inhibitory factor, granulocyte-macrophage colony stimulating factor, Fas ligand, tumor necrosis factors α and β, interferons α, β, and γ, stem cell factor, flk-2/flt3 ligand, IgG, IgM, IgA, IgD and IgE, chimeric immunoglobulins, humanized antibodies, single chain antibodies, T cell receptors, chimeric T cell receptors, single chain T cell receptors, class I and class II MHC molecules.

In one embodiment, the heterologous nucleic acid sequence encodes a protein selected from the group consisting acid alpha-glucosidase (GAA); ATP7B (copper transporting ATPase2); alpha galactosidase; ASS1 (arginosuccinate synthase); beta-glucocerebrosidase; beta-hexosaminidase A; SERPING1 (C1 protease inhibitor); glucose-6-phosphatase; erythropoietin (EPO; interferon-alpha; interferon-beta; interferon-gamma; an interleukin (IL); any one of Interleukins 1-36 (IL-1 through IL-36); interleukin (IL) receptor; a chemokine; chemokine (C-X-C motif) ligand 5 (CXCL5); granulocyte-colony stimulating factor (G-CSF); granulocyte-macrophage colony stimulating factor (GM-CSF); macrophage colony stimulating factor (M-CSF); keratinocyte growth factor (KGF); monocyte chemoattractant protein-1 (MCP-1); tumor necrosis factor (TNF); a tumor necrosis factor (TNF) receptor; alpha-1 antitrypsin; alpha-L-iduronidase; ornithine transcarbamoylase; phenylalanine hydroxylase (PAH); phenylalanine ammonia-lyase (PAL); lipoprotein lipase; an apolipoprotein; low-density lipoprotein receptor (LDL-R); albumin; lecithin cholesterol acyltransferase (LCAT); carbamoyl synthetase I; argininosuccinate synthetase; argininosuccinate lyase; arginase; fumarylacetoacetate hydrolase; porphobilinogen deaminase; cystathionine beta-synthase; branched chain ketoacid decarboxylase; isovaleryl-CoA dehydrogenase; propionyl CoA carboxylase; methylmalonyl-CoA mutase; glutaryl CoA dehydrogenase; insulin; pyruvate carboxylase; hepatic phosphorylase; phosphorylase kinase; glycine decarboxylase; H-protein, T-protein, cystic fibrosis transmembrane regulator (CFTR); ATP-binding cassette, sub-family A (ABC1), member 4 (ABCA4); and dystrophin.

DETAILED DESCRIPTION

Figure 1:
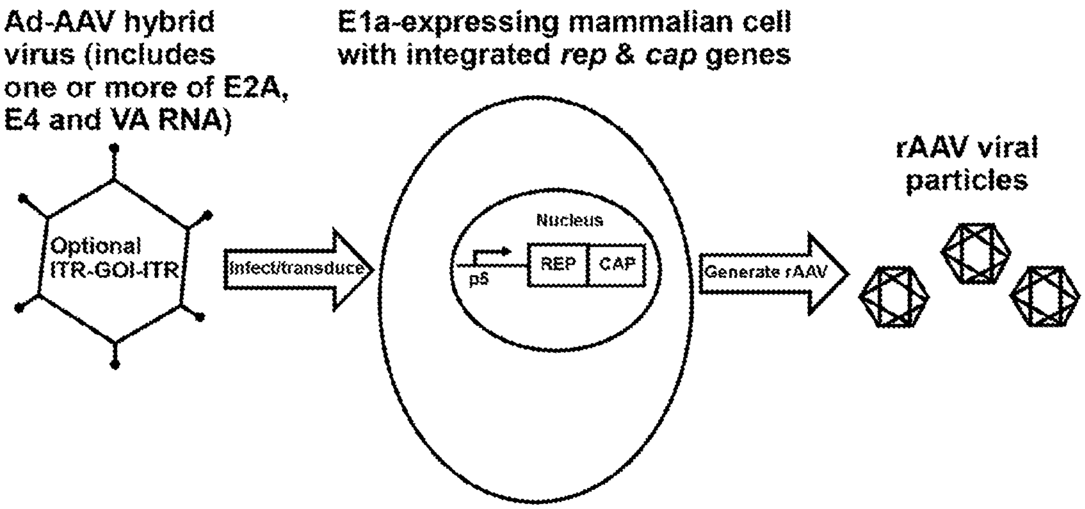
FIG. 1 shows an illustration of an Ela-expressing mammalian cell which has integrated AAV rep/cap genes, and a schematic of the process of using an Ad-AAV hybrid virus to introduce helper virus functions (adenoviral E2A and E4 proteins and VA RNA), and, optionally, a heterologous nucleic acid sequence (referred to as "GOI"), flanked by one or more AAV inverted terminal repeat (ITR) transgene). The p5 promoter is separated from the rep gene by a spacer sequence. The helper virus functions provided by the Ad-AAV hybrid virus drive rep gene expression and in turn Rep protein expression, thus permitting production of recombinant AAV (rAAV) vector particles (virions) by the cells.
Figure 2A:
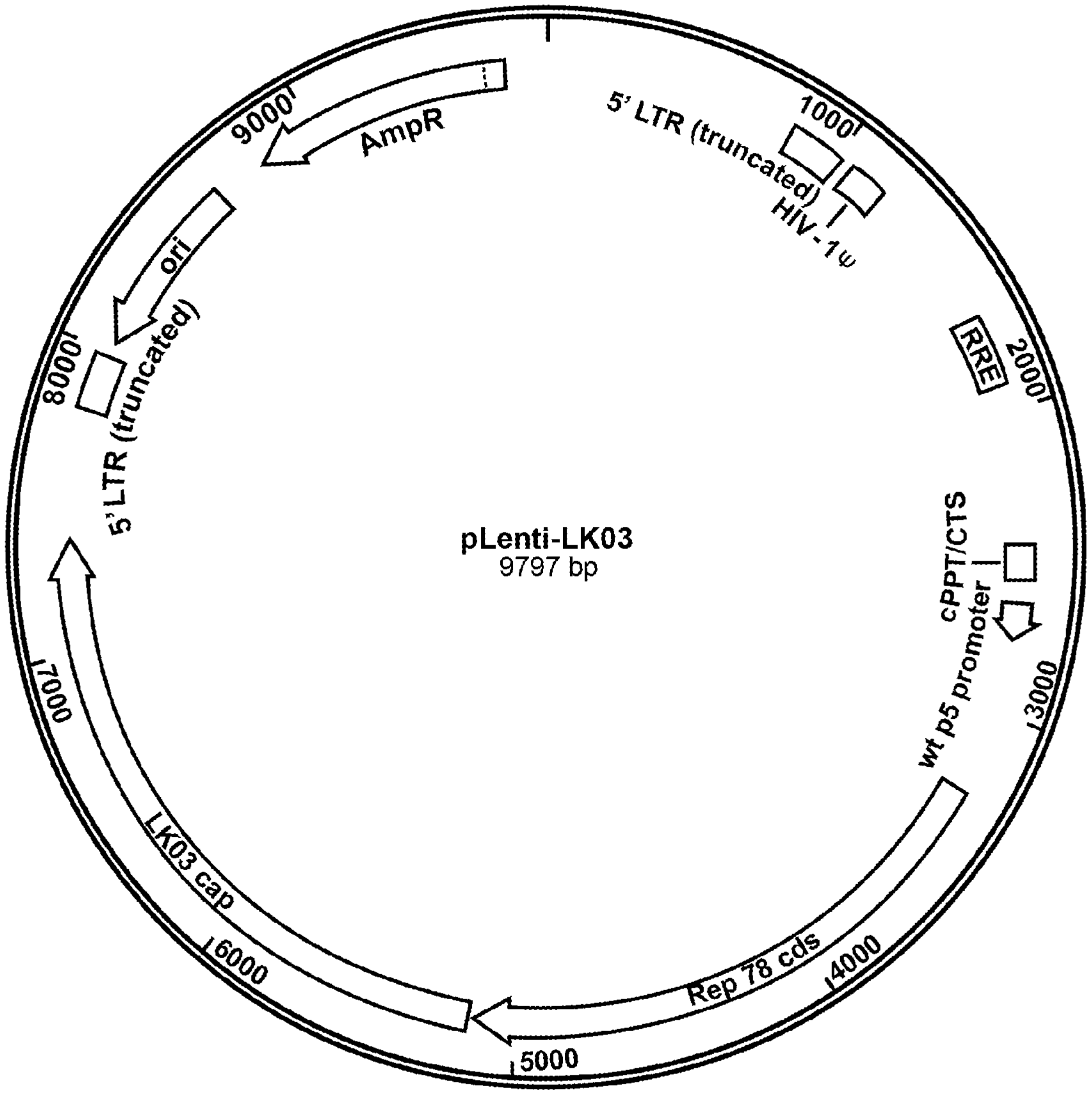
FIG. 2 shows an AAV rep/cap lentivirus shuttle vector (top) with an exemplary spacer sequence (SEQ ID NO:1) between the p5 promoter and AAV rep gene, and an exemplary Ad-AAV hybrid vector (bottom).
Figure 2B:
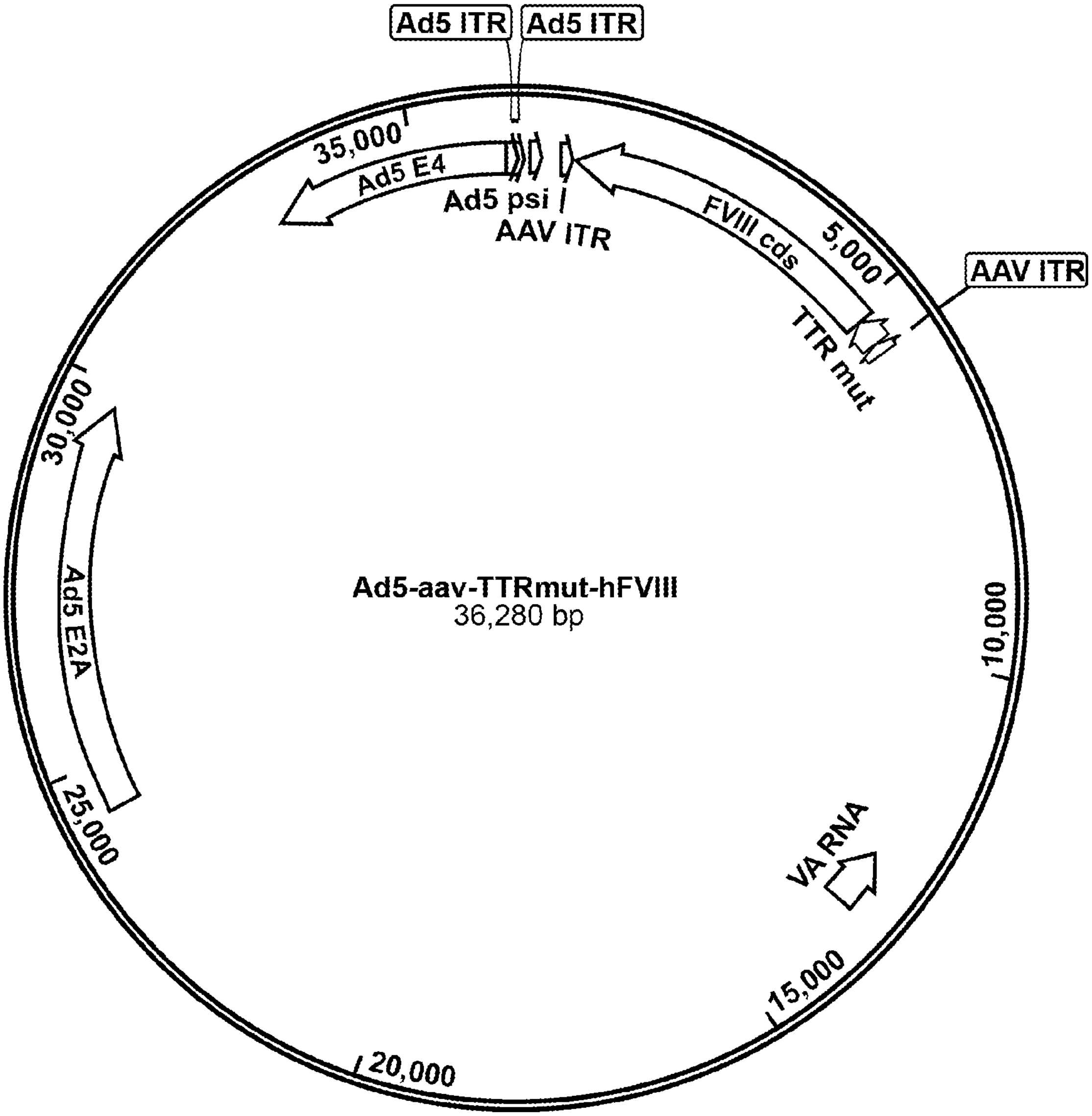
Figure 3:
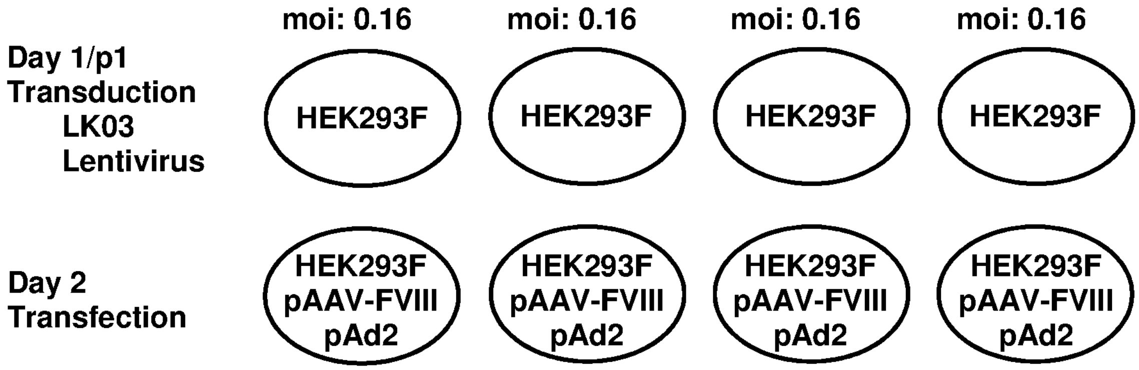
FIG. 3 shows a comparison of rAAV vector particle production with a Factor VIII heterologous nucleic acid sequence using the transient triple (3 plasmid) transfection method (+ control) or an exemplary invention cell line. The cells were produced as follows: A frozen stock of HEK293F cells was thawed, passaged once ("p1"), and plated into the wells of a tissue culture plate. One day after plating the HEK293F cells ("Day 1"), the cells were transduced with a lentivirus carrying rep/cap genes, where cap encodes LK03 (SEQ ID NO:3, "LK03 Lentivirus"), using 4 different multiplicities of infection (moi). On Day 2, the cells are transfected with two plasmids: the first plasmid carrying an expression construct for Factor VIII flanked 5' and 3' by AAV ITRs; and the second plasmid carrying Ad2 helper virus functions. Three days later, on Day 5, qPCR was carried out on DNAseI—treated cell lysate supernatants, to detect the presence of Factor VIII encoding nucleic acid, reflecting AAV vector production, and reported as vector genomes (vg)/mL.
Figure 4:
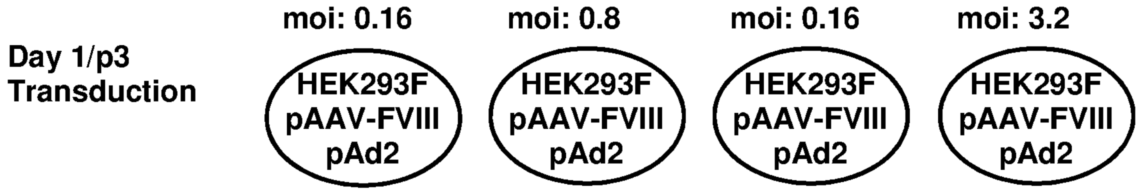
FIG. 4 shows a comparison of rAAV vector particle production with a Factor VIII heterologous nucleic acid sequence using the transient triple (3 plasmid) transfection method (+ control) or an exemplary invention cell line. This study was performed substantially as described for FIG. 3, except that the HEK293F cells were at passage 3 ("p3") after thawing. The qPCR procedure was carried out three days after the plasmid transfection and is labeled "Day 3" (rather than Day 5, which is the fifth day of the study, the same day as the study described in FIG. 4).

As understood from the literature, and as would be understood herein, "packaging" can be used to refer to cells that only have the rep and cap genes of an AAV serotype of interest, and thus are only capable of packaging rAAV virions/vectors/particles when provided with helper virus functions (typically by a helper virus such as wild type Ad5) and the heterologous nucleic acid of interest (flanked by AAV ITRs). Packaging cells can be passaged multiple times and remain viable over long periods of time. Furthermore, packaging cells can be stored under appropriate conditions, such as frozen under appropriate storage conditions, for use when needed. Thus, packaging cells are appropriate as a cell bank for the production of rAAV vector particles.

As used herein, the term "helper virus function(s)" refers to function(s) encoded in a helper virus genome which allow AAV vector genome replication and packaging (in conjunction with Rep and Cap). As disclosed herein, "helper virus function" may be provided in a number of different ways. For example, helper virus function can be provided by a virus or, for example, provided by polynucleotide sequences encoding the requisite helper function(s) to a cell in trans. In another example, a plasmid or other expression vector comprising polynucleotide sequences encoding one or more viral (e.g., adenoviral) proteins provides helper function when after transfection into a cell line of the invention along with a rAAV vector genome allows rAAV vector genome replication and packaging into rAAV vector particles.

As used herein, the term "passage" and "passages" refers to the number of times a cell culture has been subcultured, i.e., the number of times a cell culture has been harvested and reseeded into daughter cell cultures for subsequent growth. Typically, a cell line of the invention can undergo multiple passages, for example, at least 1-5, 5-10, 10-15, 15-20, or more passages without substantial cell death in the presence of expressed Ad E1A.

As used herein, the "population doubling number" is the number of doublings that a cell culture has undergone since creation or isolation. Typically, a cell line of the invention can undergo multiple doublings, for example, at least 1-5, at least 5-10, at least 10-15, at least 15-20, or at least 20 or more doublings without substantial cell death in the presence of expressed Ad E1A.

The term "producer" can be used to refer to cells that have all the components needed for packaging of rAAV vectors and can produce rAAV vector particles. Producer cells typically die over time, during rAAV production, due to rep toxicity. Due to the lack of long-term viability, producer cells are therefore not ideally suited as a cell bank.

Any mammalian cell expressing adenovirus Ela protein can be used in the invention cells and methods, including HEK293, HEK293F and PERC6 cells.

In the packaging cells of the invention, a promoter that is operably linked to the rep gene does not drive or stimulate expression of Rep protein from the rep gene because a nucleic acid spacer is positioned between the promoter and the rep gene. By inserting a nucleic acid spacer of sufficient length between a promoter and the rep gene, expression of the Rep protein is effectively attenuated, even in the presence of constitutively expressed Ela protein.

Any promoter can be used in the invention cell lines and methods. Promoters may be eukaryotic, prokaryotic or viral promoters. Promoters include non-inducible promoters and non-tissue specific promoters. In particular embodiments, the promoter is an AAV p5 promoter, which in its native state drives Rep protein expression from the rep gene. Additional nonlimiting examples of promoters include ubiquitous or promiscuous promoters/enhancers which are capable of driving expression of a polynucleotide in many different cell types. Such elements include, but are not limited to the cytomegalovirus (CMV) immediate early promoter/enhancer sequences, Rous sarcoma virus (RSV) promoter/enhancer sequences and the other viral promoters/enhancers active in a variety of mammalian cell types, or synthetic elements (see, e.g., Boshart et al., Cell, 41:521-530 (1985)), the SV40 promoter, the dihydrofolate reductase promoter, the cytoplasmic R-actin promoter and the phosphoglycerol kinase (PGK) promoter.

The nucleic acid spacer used in the invention serves the purpose of spatially moving a promoter, that is otherwise operably linked to a rep gene and drives expression of the gene, away from (distal to) the start codon of the rep gene. A "nucleic acid spacer" or "spacer" or "spacer sequence" is a polynucleotide sequence that is not transcribed, expressed, does not encode a protein, polypeptide or inhibitory nucleic acid, and is essentially inert. Spacer sequences also typically not or stem/loop structures and do not have a substantial effect on transcription other than being used to spatially separate the promoter from the rep gene. In particular embodiments, the nucleic acid spacer is positioned or located between the 3' end of an AAV p5 promoter and the 5' end of the AAV rep gene start (initiation) codon.

The presence of the spacer sequence between the promoter and the rep gene, effectively limits or prevents expression of the rep gene, even in the presence of Ela protein in the cell. The introduction of helper virus function or at least one of adenovirus E2A protein, E4 protein and/or VA RNA activates, drives or stimulates expression of the rep gene. Although not wishing to be bound by any particular mechanism, the provided helper virus functions effectively render the promoter capable of driving or stimulating expression of the rep gene even when the spacer is present.

In certain embodiments, a spacer is less than about 5000 nucleotides in length, or about 25 to about 4000 nucleotides in length, or about 250 to about 3000 nucleotides in length, or about 500 to about 2500 nucleotides in length, or about 750 to about 2400 nucleotides in length, or about 900 nucleotides to about 2300 nucleotides in length, or about 1000 nucleotides to about 2200 nucleotides in length, or about 1100 nucleotides to about 2100 nucleotides in length, or about 1200 nucleotides to about 2000 nucleotides in length, or about 1300 nucleotides to about 1900 nucleotides in length, or about 1400 nucleotides to about 1800 nucleotides in length, or about 1500 nucleotides to about 1800 nucleotides in length, or about 1600 nucleotides to about 1800 nucleotides in length, or about 1700 nucleotides to about 1800 nucleotides in length, or about 1725 nucleotides to about 1775 nucleotides in length, or about 1730 nucleotides to about 1770 nucleotides in length, or about 1740 nucleotides to about 1765 nucleotides in length, or about 1745 nucleotides to about 1760 nucleotides in length, or about 1745 nucleotides to about 1755 nucleotides in length, or about 1745 nucleotides to about 1750 nucleotides in length, or about 1746 nucleotides to about 1750 nucleotides in length, or about 1747 nucleotides to about 1750 nucleotides in length, or about 1748 nucleotides to about 1750 nucleotides in length, or about 1749 nucleotides to about 1750 nucleotides in length, or about 1749 nucleotides in length.

In certain embodiments, the spacer sequence comprises a sequence having at least about 80% identity to the sequence of SEQ ID NO:1, or at least about 85% identity to the sequence of SEQ ID NO:1, or at least about 90% identity to the sequence of SEQ ID NO:1, or at least about 95% identity to the sequence of SEQ ID NO:1, or at least about 96% identity to the sequence of SEQ ID NO:1, or at least about 97% identity to the sequence of SEQ ID NO:1, or at least about 98% identity to the sequence of SEQ ID NO:1, or at least about 99% identity to the sequence of SEQ ID NO:1.

In certain embodiments, the spacer sequence comprises a sequence having about 80% to about 100% identity to the sequence of SEQ ID NO:1, or a sequence having about 85% to about 100% identity to the sequence of SEQ ID NO:1, or a sequence having about 90% to about 100% identity to the sequence of SEQ ID NO:1, or a sequence having about 95% to about 100% identity to the sequence of SEQ ID NO:1, or a sequence having about 96% to about 100% identity to the sequence of SEQ ID NO:1, or a sequence having about 97% to about 100% identity to the sequence of SEQ ID NO:1, or a sequence having about 98% to about 100% identity to the sequence of SEQ ID NO: 1, or a sequence having about 99% to about 100% identity to the sequence of SEQ ID NO: 1.

The cells of the invention harbor a chromosomally integrated rep gene but require helper virus function in order to express Rep protein. "Helper virus" or "helper virus function" as used herein refers to at least one of adenovirus (Ad) E2A, E4 and VA RNA, or to corresponding functions of other viruses, such as herpesviruses and poxviruses, which are able to impart helper function to support replication and packaging of AAV vector genomes. In particular embodiments, a hybrid virus made of adenovirus with an E1/E3 deletion, but containing Ad E2A, E4 and VA RNA which provide helper virus function, as well as AAV ITRs flanking a heterologous nucleic acid. In other embodiments, hybrid viruses comprise helper virus functions from herpesvirus or poxvirus, along with AAV ITRs flanking a heterologous nucleic acid.

The term "vector" refers to small carrier nucleic acid molecule, a plasmid, virus (e.g., AAV vector), or other vehicle that can be manipulated by insertion or incorporation of a nucleic acid. Such vectors can be used for genetic manipulation (i.e., "cloning vectors"), to introduce/transfer polynucleotides into cells, and to transcribe or translate the inserted polynucleotide in cells. An "expression vector" is a specialized vector that contains a gene or nucleic acid sequence with the necessary regulatory regions needed for expression in a host cell. A vector nucleic acid sequence generally contains at least an origin of replication for propagation in a cell and optionally additional elements, such as a heterologous polynucleotide sequence, expression control element (e.g., a promoter, enhancer), intron, an inverted terminal repeat (ITR), selectable marker (e.g., antibiotic resistance), polyadenylation signal.

A viral vector is derived from or based upon one or more nucleic acid elements that comprise a viral genome. A particular viral vector is an adeno-associated virus (AAV) vector.

The term "recombinant," as a modifier of vector, such as recombinant AAV vector, as well as a modifier of sequences such as recombinant polynucleotides and polypeptides, means that the compositions have been manipulated (i.e., engineered) in a fashion that generally does not occur in nature. A particular example of a recombinant AAV vector would be where a click acid sequence that is not normally present in the wild-type AAV genome (e.g., a heterologous nucleic acid sequence) is inserted within the AAV genome. Although the term "recombinant" is not always used herein in reference to AAV vectors, as well as sequences such as polynucleotides, recombinant forms including polynucleotides, are expressly included in spite of any such omission.

A "recombinant AAV vector" or "rAAV" is derived from the wild type (wt or wild-type) genome of AAV by using molecular methods to remove the wild type genome from the AAV genome, and replacing with a non-native nucleic acid sequence, referred to as a heterologous nucleic acid. Typically, for AAV one or both inverted terminal repeat (ITR) sequences of AAV genome are retained in the AAV vector. rAAV is distinguished from an AAV genome, since all or a part of the AAV genome has been replaced with a non-native sequence with respect to the AAV genomic nucleic acid. Incorporation of a non-native sequence therefore defines the AAV vector as a "recombinant" vector, which can be referred to as a "rAAV vector."

A rAAV sequence can be packaged—referred to herein as a "particle"—for subsequent infection (transduction) of a cell, ex vivo, in vitro or in vivo. Where a recombinant AAV vector sequence is encapsidated or packaged into an AAV particle, the particle can also be referred to as a "rAAV vector" or "rAAV particle." Such rAAV particles include proteins that encapsidate or package the vector genome. In the case of AAV, they are referred to as capsid proteins.

A vector "genome" refers to the portion of the recombinant plasmid sequence that is ultimately packaged or encapsidated to form a viral (e.g., AAV) particle. In cases where recombinant plasmids are used to construct or manufacture recombinant vectors, the vector genome does not include the portion of the "plasmid" that does not correspond to the vector genome sequence of the recombinant plasmid. This non vector genome portion of the recombinant plasmid is referred to as the "plasmid backbone," which is important for cloning and amplification of the plasmid, a process that is needed for propagation and recombinant virus production, but is not itself packaged or encapsidated into virus (e.g., AAV) particles. Thus, a vector "genome" refers to the nucleic acid that is packaged or encapsidated by virus (e.g., AAV).

The terms "nucleic acid" and "polynucleotide" are used interchangeably herein to refer to all forms of nucleic acid, oligonucleotides, including deoxyribonucleic acid (DNA) and ribonucleic acid (RNA). Nucleic acids include genomic DNA, cDNA and antisense DNA, and spliced or unspliced mRNA, rRNA tRNA and inhibitory DNA or RNA (RNAi, e.g., small or short hairpin (sh)RNA, microRNA (miRNA), small or short interfering (si)RNA, trans-splicing RNA, or antisense RNA). Nucleic acids include naturally occurring, synthetic, and intentionally modified or altered polynucleotides (e.g., variant nucleic acid). The nucleic acids such as cDNA, genomic DNA, RNA, and fragments thereof which may be single- or double-stranded.

Polynucleotides can be single, double, or triplex, linear or circular, and can be of any length. In discussing polynucleotides, a sequence or structure of a particular polynucleotide may be described herein according to the convention of providing the sequence in the 5' to 3' direction.

A "transgene" is used herein to conveniently refer to a heterologous nucleic acid that is intended or has been introduced into a cell or organism. Transgenes include any heterologous nucleic acid, such as a gene that encodes a polypeptide or protein or encodes an inhibitory RNA.

A heterologous nucleic acid can be introduced/transferred by way of vector, such as AAV, "transduction" or "transfection" into a cell. The term "transduce" and grammatical variations thereof refer to introduction of a molecule such as an rAAV vector into a cell or host organism. The introduced heterologous nucleic acid may also exist in the recipient cell or host organism extrachromosomally, or only transiently.

A "transduced cell" is a cell into which the transgene has been introduced. Accordingly, a "transduced" cell (e.g., in a mammal, such as a cell or tissue or organ cell), means a genetic change in a cell following incorporation of an exogenous molecule, for example, a nucleic acid (e.g., a transgene) into the cell. Thus, a "transduced" cell is a cell into which, or a progeny thereof in which an exogenous nucleic acid has been introduced. The cell(s) can be propagated and the introduced protein expressed, or nucleic acid transcribed. For gene therapy uses and methods, a transduced cell can be in a subject.

An "expression control element" refers to nucleic acid sequence(s) that influence expression of an operably linked nucleic acid. Control elements, including expression control elements as set forth herein such as promoters and enhancers. Vector sequences including AAV vectors can include one or more "expression control elements." Typically, such elements are included to facilitate proper heterologous polynucleotide transcription and if appropriate translation (e.g., a promoter, enhancer, splicing signal for introns, maintenance of the correct reading frame of the gene to permit in-frame translation of mRNA and, stop codons etc.). Such elements typically act in cis, referred to as a "cis acting" element, but may also act in trans.

Expression control can be effected at the level of transcription, translation, splicing, message stability, etc. Typically, an expression control element that modulates transcription is juxtaposed near the 5' end (i.e., "upstream") of a transcribed nucleic acid. Expression control elements can also be located at the 3' end (i.e., "downstream") of the transcribed sequence or within the transcript (e.g., in an intron).

Functionally, expression of operably linked nucleic acid is at least in part controllable by the element (e.g., promoter) such that the element modulates transcription of the nucleic acid and, as appropriate, translation of the transcript. A specific example of an expression control element is a promoter, which is usually located 5' of the transcribed nucleic acid sequence. A promoter typically increases an amount expressed from operably linked nucleic acid as compared to an amount expressed when no promoter exists.

An "enhancer" as used herein can refer to a sequence that is located adjacent to the heterologous nucleic acid. Enhancer elements are typically located upstream of a promoter element but also function and can be located downstream of or within a sequence. Enhancer elements typically increase expressed of an operably linked nucleic acid above expression afforded by a promoter element.

Expression control elements herein, such as promoters, are typically positioned at a distance away from the transcribed sequence. In particular embodiments, an expression control element such as a promoter is positioned at least about 25 nucleotides 5' of the rep gene start codon, is positioned about 25-5,000 nucleotides 5' of the rep gene start codon, is positioned about 250-2,500 nucleotides 5' of the rep gene start codon, is positioned about 500-2,000 nucleotides 5' of the rep gene start codon, is positioned about 1,000-1,900 nucleotides 5' of the rep gene start codon, is positioned about 1,500-1,900 nucleotides 5' of the rep gene start codon, is positioned about 1,600-1,800 nucleotides 5' of the rep gene start codon, is positioned about 1,700-1,800 nucleotides 5' of the rep gene start codon, or is positioned about 1,750 nucleotides 5' of the rep gene start codon.

Expression control elements include ubiquitous or promiscuous promoters/enhancers which are capable of driving expression of a polynucleotide in many different cell types. Such elements include, but are not limited to the cytomegalovirus (CMV) immediate early promoter/enhancer sequences, the Rous sarcoma virus (RSV) promoter/enhancer sequences and the other viral promoters/enhancers active in a variety of mammalian cell types, or synthetic elements (see, e.g., Boshart et al., *Cell,* 41:521-530 (1985)), the SV40 promoter, the dihydrofolate reductase promoter, the cytoplasmic β-actin promoter and the phosphoglycerol kinase (PGK) promoter.

Expression control elements also include the native elements(s) for the heterologous polynucleotide. A native control element (e.g., promoter) may be used when it is desired that expression of the heterologous polynucleotide should mimic the native expression. Other native control elements, such as introns, polyadenylation sites or Kozak consensus sequences may also be used.

The term "operably linked" means that the regulatory sequences necessary for expression of a nucleic acid sequence are placed in the appropriate positions relative to the sequence so as to effect expression of the nucleic acid sequence. This same definition is sometimes applied to the arrangement of nucleic acid sequences and transcription control elements (e.g. promoters, enhancers, and termination elements) in an expression vector, e.g., rAAV vector.

In the example of an expression control element in operable linkage with a nucleic acid, the relationship is such that the control element modulates expression of the nucleic acid. More specifically, for example, two DNA sequences operably linked means that the two DNAs are arranged (cis or trans) in such a relationship that at least one of the DNA sequences is able to exert a physiological effect upon the other sequence.

As disclosed herein, a nucleic acid spacer sequence positioned between an expression control element and an AAV rep gene can substantially reduce or eliminate expression of the rep gene thereby in turn reducing or eliminating expression of the Rep protein and allowing cells to survive even while the cells also express adenovirus E1A protein. Addition of helper virus function to such cells, such as provided by a hybrid virus, adenovirus, poxvirus or herpesvirus, can overcome the attenuating effect of the spacer nucleic acid on rep gene expression and in turn drive expression of rep gene thereby providing Rep protein expression.

Additional elements for rAAV vectors include, without limitation, a transcription termination signal or stop codon, 5' or 3' untranslated regions (e.g., polyadenylation (polyA) sequences) which flank a sequence, such as one or more copies of an AAV ITR sequence, or an intron.

Further elements include, for example, filler or stuffer polynucleotide sequences, for example to improve packaging and reduce the presence of contaminating nucleic acid. AAV vectors typically accept inserts of DNA having a size range which is generally about 4 kb to about 5.2 kb, or slightly more. Thus, for shorter sequences, inclusion of a stuffer or filler in order to adjust the length to near or at the normal size of the virus genomic sequence acceptable for AAV vector packaging into virus particle. In various embodiments, a filler/stuffer nucleic acid sequence is an untranslated (non-protein encoding) segment of nucleic acid. For a nucleic acid sequence less than 4.7 kb, the filler or stuffer polynucleotide sequence has a length that when combined (e.g., inserted into a vector) with the sequence has a total length between about 3.0-5.5 kb, or between about 4.0-5.0 kb, or between about 4.3-4.8 kb.

Where a wild type heterologous nucleic acid or transgene is too large to be packaged within an AAV vector particle, the heterologous nucleic acid may be provided in modified, fragmented or truncated form for packaging in and delivery by an AAV vector, such that a functional protein or nucleic acid product, such as a therapeutic protein or nucleic acid product, is ultimately provided.

In some embodiments, the heterologous nucleic acid that encodes a protein (e.g., therapeutic protein) is provided in modified or truncated forms or the heterologous nucleic acid is provided in multiple constructs, delivered by separate and multiple AAV vectors.

In certain aspects, the heterologous nucleic acid is provided as a truncated variant that maintains functionality of the encoded protein (e.g., therapeutic protein), including removal of portions unnecessary for function, such that the encoding heterologous polynucleotide is reduced in size for packaging in an AAV vector.

In certain aspects the heterologous nucleic acid is provided in split AAV vectors, each providing nucleic acid encoding different portions of a protein (e.g., therapeutic protein), thus delivering multiple portions of a protein (e.g., therapeutic protein) which assemble and function in the cell.

In other aspects, the heterologous nucleic acid is provided by dual AAV vectors using overlapping, trans-splicing or hybrid trans-splicing dual vector technology. In certain embodiments, two overlapping AAV vectors are used which combine in the cell to generate a full expression cassette, from which a full-length protein (e.g., therapeutic protein) is expressed.

A "hemostasis related disorder" refers to bleeding disorders such as hemophilia A, hemophilia A with inhibitory antibodies, hemophilia B, hemophilia B with inhibitory antibodies, a deficiency in any coagulation Factor: VII, VIII, IX, X, XI, V, XII, II, von Willebrand factor, combined FV/FVIII deficiency, thalassemia, vitamin K epoxide reductase C1 deficiency, or gamma-carboxylase deficiency; bleeding associated with trauma, injury, thrombosis, thrombocytopenia, stroke, coagulopathy, or disseminated intravascular coagulation (DIC); over-anticoagulation associated with heparin, low molecular weight heparin, pentasaccharide, warfarin, or small molecule antithrombotics (i.e., FXa inhibitors); and platelet disorders such as, Bernard Soulier syndrome, Glanzmann thrombasthenia, and storage pool deficiency.

The term "isolated," when used as a modifier of a composition, means that the compositions are made by the hand of man or are separated, completely or at least in part, from their naturally occurring in vivo environment. Generally, isolated compositions are substantially free of one or more materials with which they normally associate with in nature, for example, one or more protein, nucleic acid, lipid, carbohydrate, cell membrane.

The term "isolated" does not exclude combinations produced by the hand of man, for example, a rAAV sequence, or rAAV particle that packages or encapsidates an AAV vector genome and a pharmaceutical formulation. The term "isolated" also does not exclude alternative physical forms of the composition, such as hybrids/chimeras, multimers/oligomers, modifications (e.g., phosphorylation, glycosylation, lipidation) or derivatized forms, or forms expressed in host cells produced by the hand of man.

The term "substantially pure" refers to a preparation comprising at least 50-60% by weight the compound of interest (e.g., nucleic acid, oligonucleotide, protein, etc.). The preparation can comprise at least 75% by weight, or at least 85% by weight, or about 90-99% by weight, of the compound of interest. Purity is measured by methods appropriate for the compound of interest (e.g., chromatographic methods, agarose or polyacrylamide gel electrophoresis, HPLC analysis, and the like).

The phrase "consisting essentially of" when referring to a particular nucleotide sequence or amino acid sequence means a sequence having the properties of a given SEQ ID NO. For example, when used in reference to an amino acid sequence, the phrase includes the sequence per se and molecular modifications that would not affect the basic and novel characteristics of the sequence.

The term "identity," "homology" and grammatical variations thereof, mean that two or more referenced entities are the same, when they are "aligned" sequences. Thus, by way of example, when two protein sequences are identical, they have the same amino acid sequence, at least within the referenced region or portion. Where two nucleic acid sequences are identical, they have the same nucleic acid sequence, at least within the referenced region or portion. The identity can be over a defined area (region or domain) of the sequence.

An "area" or "region" of identity refers to a portion of two or more referenced entities that are the same. Thus, where two protein or nucleic acid sequences are identical over one or more sequence areas or regions they share identity within that region. An "aligned" sequence refers to multiple protein (amino acid) or nucleic acid sequences, often containing corrections for missing or additional bases or amino acids (gaps) as compared to a reference sequence.

The identity can extend over the entire length or a portion of the sequence. In certain embodiments, the length of the sequence sharing the percent identity is 2, 3, 4, 5 or more contiguous amino acids or nucleic acids, e.g., 6, 7, 8, 9, 10, 11, 12, 13, 14, 15, 16, 17, 18, 19, 20, etc. contiguous nucleic acids or amino acids. In additional embodiments, the length of the sequence sharing identity is 21 or more contiguous amino acids or nucleic acids, e.g., 21, 22, 23, 24, 25, 26, 27, 28, 29, 30, 31, 32, 33, 34, 35, 36, 37, 38, 39, 40, etc. contiguous amino acids or nucleic acids. In further embodiments, the length of the sequence sharing identity is 41 or more contiguous amino acids or nucleic acids, e.g., 42, 43, 44, 45, 45, 47, 48, 49, 50, etc., contiguous amino acids or nucleic acids. In yet further embodiments, the length of the sequence sharing identity is 50 or more contiguous amino acids or nucleic acids, e.g., 50-55, 55-60, 60-65, 65-70, 70-75, 75-80, 80-85, 85-90, 90-95, 95-100, 100-150, 150-200, 200-250, 250-300, 300-500, 500-1,000, etc. contiguous amino acids or nucleic acids.

The extent of identity (homology) or "percent identity" between two sequences can be ascertained using a computer program and/or mathematical algorithm. For purposes of this invention comparisons of nucleic acid sequences are performed using the GCG Wisconsin Package version 9.1, available from the Genetics Computer Group in Madison, Wisconsin For convenience, the default parameters (gap creation penalty=12, gap extension penalty=4) specified by that program are intended for use herein to compare sequence identity. Alternately, the Blastn 2.0 program provided by the National Center for Biotechnology Information (found on the world wide web at ncbi.nlm.nih.gov/blast/; Altschul et al., 1990, J Mol Biol 215:403-410) using a gapped alignment with default parameters, may be used to determine the level of identity and similarity between nucleic acid sequences and amino acid sequences. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate extent of identity (Pearson et al., Proc. Natl. Acad. Sci. USA 85:2444 (1988); Pearson, Methods Mol Biol. 132:185 (2000); and Smith et al., J. Mol. Biol. 147:195 (1981)). Programs for quantitating protein structural similarity using Delaunay-based topological mapping have also been developed (Bostick et al., Biochem Biophys Res Commun. 304:320 (2003)).

Nucleic acid molecules, expression vectors (e.g., AAV vector genomes), plasmids, including nucleic acid encoding modified/variant AAV capsids of the invention and heterologous nucleic acids may be prepared by using recombinant DNA technology methods. The availability of nucleotide sequence information enables preparation of isolated nucleic acid molecules of the invention by a variety of means. For example, nucleic acid sequences can be made using various standard cloning, recombinant DNA technology, via cell expression or in vitro translation and chemical synthesis techniques. Purity of polynucleotides can be determined through sequencing, gel electrophoresis and the like. For example, nucleic acids can be isolated using hybridization or computer-based database screening techniques. Such techniques include, but are not limited to: (1) hybridization of genomic DNA or cDNA libraries with probes to detect homologous nucleotide sequences; (2) antibody screening to detect polypeptides having shared structural features, for example, using an expression library; (3) polymerase chain reaction (PCR) on genomic DNA or cDNA using primers capable of annealing to a nucleic acid sequence of interest; (4) computer searches of sequence databases for related sequences; and (5) differential screening of a subtracted nucleic acid library.

Nucleic acids may be maintained as DNA in any convenient cloning vector. Clones can be maintained in a plasmid cloning/expression vector, such as pBluescript (Stratagene, La Jolla, CA), which is propagated in a suitable *E. coli* host cell. Alternatively, nucleic acids may be maintained in vector suitable for expression in mammalian cells, for example, an AAV vector. In cases where post-translational modification affects coagulation function, nucleic acid molecule can be expressed in mammalian cells.

As disclosed herein, rAAV vectors may optionally comprise regulatory elements necessary for expression of the heterologous nucleic acid in a cell positioned in such a manner as to permit expression of the encoded protein in the host cell. Such regulatory elements required for expression include, but are not limited to, promoter sequences, enhancer sequences and transcription initiation sequences as set forth herein and known to the skilled artisan.

The rAAV vectors are useful in methods of delivering, administering or providing sequence encoded by heterologous nucleic acid to a subject in need thereof, as a method of treatment. In this manner, the nucleic acid is transcribed and a protein or inhibitory nucleic acid may be produced in vivo in a subject. The subject may benefit from or be in need of the protein or inhibitory nucleic acid because the subject has a deficiency of the protein, or because production of the protein or inhibitory nucleic acid in the subject may impart some therapeutic effect, as a method of treatment or otherwise. For example, an inhibitory nucleic acid can reduce expression or transcription of an aberrant deleterious protein that is expressed in a subject in which the apparent or deleterious protein causes a disease or disorder, such as a neurological disease or disorder.

rAAV vectors comprising an AAV genome with a heterologous nucleic acid permit the treatment of genetic diseases. For deficiency state diseases, gene transfer can be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. The use of site-specific integration of nucleic acid sequences to correct defects is also possible.

In various embodiments, rAAV vectors comprising an AAV genome with a heterologous nucleic acid may be used, for example, as therapeutic and/or prophylactic agents (protein or nucleic acid). In particular embodiments, the heterologous nucleic acid encodes a protein that can modulate the blood coagulation cascade.

For example, an encoded FVIII or hFVIII-BDD may have similar coagulation activity as wild-type FVIII, or altered coagulation activity compared to wild-type FVII. Administration of FVIII- or hFVIII-BDD-encoding rAAV vectors to a patient with hemophilia A results in the expression of FVIII or hFVIII-BDD protein which serves to normalize the coagulation cascade.

In additional embodiments, a heterologous nucleic acid encodes a protein (enzyme) that can inhibit or reduce the accumulation of glycogen, prevent the accumulation of glycogen or degrade glycogen. For example, an encoded GAA may have similar activity as wild-type GAA. Administration of GAA-encoding rAAV vectors to a patient with Pompe disease results in the expression of the GAA protein which serves to inhibit or reduce the accumulation of glycogen, prevent the accumulation of glycogen or degrade glycogen, which in turn can reduce or decrease one or more adverse effects of Pompe disease.

Non-limiting examples of diseases treatable with rAAV vectors include lung disease (e.g., cystic fibrosis), a bleeding disorder (e.g., hemophilia A or hemophilia B with or without inhibitors), thalassemia, a blood disorder (e.g., anemia), Alzheimer's disease, Parkinson's disease, Huntington's disease, amyotrophic lateral sclerosis (ALS), epilepsy, a lysosomal storage disease (e.g., aspartylglucosaminuria, Batten disease, late infantile neuronal ceroid lipofuscinosis type 2 (CLN2), cystinosis, Fabry disease, Gaucher disease types I, II, and III, glycogen storage disease II (Pompe disease), ganglioside monosialic 2 (GM2)-gangliosidosis type I (Tay Sachs disease), GM2-gangliosidosis type II (Sandhoff disease), mucolipidosis types I (sialidosis type I and II), II (I-cell disease), III (pseudo-Hurler disease) and IV, mucopolysaccharide storage diseases (Hurler disease and variants, Hunter, Sanfilippo Types A, B, C, D, Morquio Types A and B, Maroteaux-Lamy and Sly diseases), Niemann-Pick disease types A/B, C1 and C2, and Schindler disease types I and II), hereditary angioedema (HAE), a copper or iron accumulation disorder (e.g., Wilson's or Menkes disease), lysosomal acid lipase deficiency, a neurological or neurodegenerative disorder, cancer, type 1 or type 2 diabetes, adenosine deaminase deficiency, a metabolic defect (e.g., glycogen storage diseases), a disease of solid organs (e.g., brain, liver, kidney, heart), or an infectious viral (e.g., hepatitis B and C, human immunodeficiency virus (HIV), etc.), bacterial or fungal disease.

Additional non-limiting examples of diseases treatable with rAAV vectors include hemostasis related disorders or bleeding disorders such as hemophilia A, hemophilia A with inhibitory antibodies, hemophilia B, hemophilia B with inhibitory antibodies, a deficiency in any coagulation Factor: VII, VIII, IX, X, XI, V, XII, II, von Willebrand factor, combined FV/FVIII deficiency, thalassemia, vitamin K epoxide reductase C1 deficiency, or gamma-carboxylase deficiency; bleeding associated with trauma, injury, thrombosis, thrombocytopenia, stroke, coagulopathy, or disseminated intravascular coagulation (DIC); over-anticoagulation associated with heparin, low molecular weight heparin, pentasaccharide, warfarin, or small molecule antithrombotics (i.e., FXa inhibitors); and platelet disorders such as, Bernard Soulier syndrome, Glanzmann thrombasthenia, and storage pool deficiency.

Non-limiting examples of heterologous nucleic acids encoding gene products (e.g., therapeutic proteins) useful in accordance with the invention include, but are not limited to GAA (acid alpha-glucosidase) for treatment of Pompe disease; TPP1 (tripeptidyl peptidase-1) for treatment of late infantile neuronal ceroid lipofuscinosis type 2 (CLN2), ATP7B (copper transporting ATPase2) for treatment of Wilson's disease; alpha galactosidase for treatment of Fabry disease; ASS1 (arginosuccinate synthase) for treatment of citrullinemia type 1; beta-glucocerebrosidase for treatment of Gaucher disease type 1; beta-hexosaminidase A for treatment of Tay Sachs disease; SERPING1 (C1 protease inhibitor; C1 esterase inhibitor) for treatment of hereditary angioedema (HAE); glucose-6-phosphatase for treatment of glycogen storage disease type I (GSDI); erythropoietin (EPO) for treatment of anemia; interferon-alpha, interferon-beta, and interferon-gamma for treatment of various immune disorders, viral infections and cancer; an interleukin (IL), including any one of IL-1 through IL-36, and corresponding receptors, for treatment of various inflammatory diseases or immuno-deficiencies; a chemokine, including chemokine (C-X-C motif) ligand 5 (CXCL5) for treatment of immune disorders; granulocyte-colony stimulating factor (G-CSF) for treatment of immune disorders such as Crohn's disease; granulocyte-macrophage colony stimulating factor (GM-CSF) for treatment of various human inflammatory diseases; macrophage colony stimulating factor (M-CSF) for treatment of various human inflammatory diseases; keratinocyte growth factor (KGF) for treatment of epithelial tissue damage; chemokines such as monocyte chemoattractant protein-1 (MCP-1) for treatment of recurrent miscarriage, HIV-related complications, and insulin resistance; tumor necrosis factor (TNF) and receptors for treatment of various immune disorders; alphal-antitrypsin for treatment of emphysema or chronic obstructive pulmonary disease (COPD); alpha-L-iduronidase for treatment of mucopolysaccharidosis I (MPS I); ornithine transcarbamoylase (OTC) for treatment of OTC deficiency; phenylalanine hydroxylase (PAH) or phenylalanine ammonia-lyase (PAL) for treatment of phenylketonuria (PKU); lipoprotein lipase for treatment of lipoprotein lipase deficiency; apolipoproteins for treatment of apolipoprotein (Apo) A-I deficiency; low-density lipoprotein receptor (LDL-R) for treatment of familial hypercholesterolemia (FH); albumin for treatment of hypoalbuminemia; lecithin cholesterol acyltransferase (LCAT); carbamoyl synthetase I; argininosuccinate synthetase; argininosuccinate lyase; arginase; fumarylacetoacetate hydrolase; porphobilinogen deaminase; cystathionine beta-synthase for treatment of homocystinuria; branched chain ketoacid decarboxylase; isovaleryl-CoA dehydrogenase; propionyl CoA carboxylase; methylmalonyl-CoA mutase; glutaryl CoA dehydrogenase; insulin; pyruvate carboxylase; hepatic phosphorylase; phosphorylase kinase; glycine decarboxylase; H-protein; T-protein; cystic fibrosis transmembrane regulator (CFTR); ATP-binding cassette, sub-family A (ABC1), member 4 (ABCA4) for the treatment of Stargardt disease; and dystrophin.

In further embodiments, a heterologous polynucleotide encodes an antibody, β-globin, α-globin, spectrin, a metal transporter (ATP7A or ATP7), sulfamidase, arylsulfatase A (cerebroside-sulfatase; ARSA), hypoxanthine guanine phosphoribosyl transferase, β-25 glucocerebrosidase, sphingomyelinase, lysosomal hexosaminidase, branched-chain keto acid dehydrogenase, a hormone, a growth factor, insulin-like growth factor 1 or 2, platelet derived growth factor, epidermal growth factor, nerve growth factor, neurotrophic factor-3 and -4, brain-derived neurotrophic factor, glial derived growth factor, transforming growth factor α, transforming growth factor β, a cytokine, α-interferon, β-interferon, interferon-γ, interleukin-2, interleukin-4, interleukin-12, granulocyte-macrophage colony stimulating factor, lymphotoxin, a suicide gene product, herpes simplex virus thymidine kinase, cytosine deaminase, diphtheria toxin, cytochrome P450, deoxycytidine kinase, tumor necrosis factor, a drug resistance protein, a tumor suppressor protein (e.g., p53, Rb, Wt-1, NF1, Von Hippel-Lindau (VHL), adenomatous polyposis coli (APC)), a peptide with immunomodulatory properties, a tolerogenic or immunogenic peptide or protein Tregitope or hCDR1, glucokinase, guanylate cyclase 2D (LCA-GUCY2D), retinal pigment epithelium-specific 65 kDa protein (RPE65), Rab escort protein 1 (choroideremia), LCA 5 (LCA-lebercilin), ornithine ketoacid aminotransferase (gyrate atrophy), retinoschisin 1 (X-linked retinoschisis), USH1C (Usher's syndrome 1C), X-linked retinitis pigmentosa GTPase, MER proto-oncogene tyrosine kinase (MERTK), ABCA4, DFNB1 (connexin 26 deafness), ACHM 2, 3 and 4 (achromatopsia), PKD-1 or PKD-2 (polycystic kidney disease), a sulfatase, N-acetylglucosamine-1-phosphate transferase, cathepsin A, GM2-AP, NPC1, VPC2, a sphingolipid activator protein, one or more zinc finger nuclease for genome editing, and one or more donor sequence used as repair templates for genome editing.

In certain embodiments, the protein encoded by a heterologous polynucleotide comprises a gene editing nuclease. In certain aspects, the gene editing nuclease comprises a zinc finger nuclease (ZFN) or a transcription activator-like effector nuclease (TALEN). In certain aspects, the gene editing nuclease comprises a functional Type II CRISPR-Cas9.

In certain embodiments, a heterologous polynucleotide encodes an inhibitory nucleic acid. In certain aspects, the inhibitory nucleic acid is selected from the group consisting of a siRNA, an antisense molecule, miRNA, RNAi, a ribozyme and a shRNA. In certain aspects, the inhibitory nucleic acid binds to a gene, a transcript of a gene, or a transcript of a gene associated with a polynucleotide repeat disease including, but not limited to, a huntingtin (HTT) gene, a gene associated with dentatorubropallidoluysian atrophy (atrophin 1, ATN1), androgen receptor on the X chromosome in spinobulbar muscular atrophy, human Ataxin-1, -2, -3, and -7, Cav2.1 P/Q voltage-dependent calcium channel (CACNA1A), TATA-binding protein, Ataxin 8 opposite strand (ATXN8OS), Serine/threonine-protein phosphatase 2A 55 kDa regulatory subunit B beta isoform in spinocerebellar ataxia (type 1, 2, 3, 6, 7, 8, 12 17), FMR1 (fragile X mental retardation 1) in fragile X syndrome, FMR1 (fragile X mental retardation 1) in fragile X-associated tremor/ataxia syndrome, FMR1 (fragile X mental retardation 2) or AF4/FMR2 family member 2 in fragile XE mental retardation; myotonin-protein kinase (MT-PK) in myotonic dystrophy; frataxin in Friedreich's ataxia; a mutant of superoxide dismutase 1 (SOD1) gene in amyotrophic lateral sclerosis; a gene involved in pathogenesis of Parkinson's disease and/or Alzheimer's disease; apolipoprotein B (APOB) and proprotein convertase subtilisin/kexin type 9 (PCSK9), hypercholesterolemia; HIV Tat, human immunodeficiency virus transactivator of transcription gene, in HIV infection; HIV TAR, HIV TAR, human immunodeficiency virus transactivator response element gene, in HIV infection; C-C chemokine receptor 5 (CCR5) in HIV infection; Rous sarcoma virus (RSV) nucleocapsid protein in RSV infection, liver-specific microRNA (miR-122) in hepatitis C virus infection; p53, acute kidney injury or delayed graft function kidney transplant or kidney injury acute renal failure; protein kinase N3 (PKN3) in advance recurrent or metastatic solid malignancies; LMP2, LMP2 also known as proteasome subunit beta-type 9 (PSMB 9), metastatic melanoma; LMP7, also known as proteasome subunit beta-type 8 (PSMB 8), metastatic melanoma; MECL1 also known as proteasome subunit beta-type 10 (PSMB 10), metastatic melanoma; vascular endothelial growth factor (VEGF) in solid tumors; kinesin spindle protein in solid tumors, apoptosis suppressor B-cell CLL/lymphoma (BCL-2) in chronic myeloid leukemia; ribonucleotide reductase M2 (RRM2) in solid tumors; Furin in solid tumors; polo-like kinase 1 (PLK1) in liver tumors, diacylglycerol acyltransferase 1 (DGAT1) in hepatitis C infection, beta-catenin in familial adenomatous polyposis; beta2 adrenergic receptor, glaucoma; RTP801/Redd1 also known as DAN damage-inducible transcript 4 protein, in diabetic macular edema (DME) or age-related macular degeneration; vascular endothelial growth factor receptor I (VEGFR1) in age-related macular degeneration or choroidal neovascularization, caspase 2 in non-arteritic ischaemic optic neuropathy; keratin 6A N17K mutant protein in pachyonychia congenital; influenza A virus genome/gene sequences in influenza infection; severe acute respiratory syndrome (SARS) coronavirus genome/gene sequences in SARS infection; respiratory syncytial virus genome/gene sequences in respiratory syncytial virus infection; Ebola filovirus genome/gene sequence in Ebola infection; hepatitis B and C virus genome/gene sequences in hepatitis B and C infection; herpes simplex virus (HSV) genome/gene sequences in HSV infection, coxsackievirus B3 genome/gene sequences in coxsackievirus B3 infection; silencing of a pathogenic allele of a gene (allele-specific silencing) like torsin A (TOR1A) in primary dystonia, pan-class I and human leukocyte antigen (HLA)-allele specific in transplant; and mutant rhodopsin gene (RHO) in autosomal dominantly inherited retinitis pigmentosa (adRP).

rAAV vectors may be administered alone, or in combination with or more compound, agent, drug, treatment or other therapeutic regimen or protocol having a desired therapeutic, beneficial, additive, synergistic or complementary activity or effect. Exemplary combination compositions and treatments include second actives, such as, biologics (proteins), agents (e.g., immunosuppressive agents) and drugs. Such biologics (proteins), agents, drugs, treatments and therapies can be administered or performed prior to, substantially contemporaneously with or following any other method or use of the invention, for example, a therapeutic method of treating a subject for a blood clotting disease such as hemophilia A or a lysosomal storage disease such as Pompe disease.

According to the invention, rAAV vectors or a combination of therapeutic agents may be administered to a subject or patient alone or in a pharmaceutically acceptable or biologically compatible composition.

As set forth herein, rAAV are useful as gene therapy vectors as they can penetrate cells and introduce nucleic acid/genetic material into the cells. Because AAV are not associated with pathogenic disease in humans, rAAV vectors are able to deliver heterologous polynucleotide sequences (e.g., therapeutic proteins and agents) to human patients without causing substantial AAV pathogenesis or disease.

rAAV vectors possess a number of desirable features for such applications, including tropism for dividing and non-dividing cells. Early clinical experience with these vectors also demonstrated no sustained toxicity and immune responses were minimal or undetectable. AAV are known to infect a wide variety of cell types in vivo and in vitro by receptor-mediated endocytosis or by transcytosis. These vector systems have been tested in humans targeting many tissues, such as, retinal epithelium, liver, skeletal muscle, airways, brain, joints and hematopoietic stem cells.

It may be desirable to introduce a rAAV vector that can provide, for example, multiple copies of a desired gene and hence greater amounts of the product of that gene. Improved rAAV vectors and methods for producing these vectors have been described in detail in a number of references, patents and patent applications, including: Wright J. F. (Hum Gene Ther 20:698-706, 2009).

Recombinant AAV vector, as well as methods and uses thereof, include any viral strain or serotype. As a non-limiting example, a recombinant AAV vector can be based upon any AAV genome, such as LK03 (SEQ ID NO:3), Spk100 (SEQ ID NO:4), AAV-1, -2, -3, -4, -5, -6, -7, -8, -9, -10, -11, -12, -rh74, -rh10 or AAV3B, for example. Such vectors can be based on the same strain or serotype (or subgroup or variant) or be different from each other. As a non-limiting example, a recombinant AAV vector based upon a particular serotype genome can be identical to the serotype of the capsid proteins that package the vector. In addition, a recombinant AAV vector genome can be based upon an AAV serotype genome distinct from the serotype of the AAV capsid proteins that package the vector. For example, the AAV vector genome can be based upon AAV2, whereas at least one of the three capsid proteins could be a LK03 (SEQ ID NO:3), Spk100 (SEQ ID NO:4), AAV1, AAV3, AAV4, AAV5, AAV6, AAV7, AAV8, AAV9, AAV10, AAV11, AAV12, Rh10, Rh74, AAV3B or AAV-2i8 as well as variants thereof as disclosed herein, for example. Such AAV capsid variants include the variants of AAV capsids set forth in WO2012/145601, WO2013/158879, WO2015/013313, WO2018/156654, US2013/0059732, U.S. Pat. Nos. 9,169,299, 7,749,492, and 9,587,282.

As used herein, the term "serotype" is a distinction used to refer to an AAV having a capsid that is serologically distinct from other AAV serotypes. Serologic distinctiveness is determined on the basis of the lack of cross-reactivity between antibodies to one AAV as compared to another AAV. Such cross-reactivity differences are usually due to differences in capsid protein sequences/antigenic determinants (e.g., due to VP1, VP2, and/or VP3 sequence differences of AAV serotypes). Despite the possibility that AAV variants including capsid variants may not be serologically distinct from a reference AAV or other AAV serotype, they differ by at least one nucleotide or amino acid residue compared to the reference or other AAV serotype.

Under the traditional definition, a serotype means that the virus of interest has been tested against serum specific for all existing and characterized serotypes for neutralizing activity and no antibodies have been found that neutralize the virus of interest. As more naturally occurring virus isolates of are discovered and/or capsid mutants generated, there may or may not be serological differences with any of the currently existing serotypes. Thus, in cases where the new virus (e.g., AAV) has no serological difference, this new virus (e.g., AAV) would be a subgroup or variant of the corresponding serotype. In many cases, serology testing for neutralizing activity has yet to be performed on mutant viruses with capsid sequence modifications to determine if they are of another serotype according to the traditional definition of serotype. Accordingly, for the sake of convenience and to avoid repetition, the term "serotype" broadly refers to both serologically distinct viruses (e.g., AAV) as well as viruses (e.g., AAV) that are not serologically distinct that may be within a subgroup or a variant of a given serotype.

As set forth herein, AAV capsid proteins and nucleic acids encoding the capsid proteins include those with less than 100% sequence identity to a reference or parental AAV serotype such as LK03 (SEQ ID NO:3), Spk100 (SEQ ID NO:4), AAV1, AAV2, AAV3, AAV4, AAV5, AAV6, AAV7, AAV8, AAV9, AAV10, AAV11, AAV12, Rh10, Rh74 AAV3B or AAV-2i8. In one embodiment, a modified/variant AAV capsid protein includes or consists of a sequence at least 75% or more identical to, such as 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 99.9% identical to a reference or parental AAV capsid protein, such as LK03 (SEQ ID NO:3), Spk100 (SEQ ID NO:4), AAV1, AAV2, AAV3, AAV4, AAV5, AAV6, AAV7, AAV8, AAV9, AAV10, AAV11, AAV12, Rh10, Rh74, AAV3B or AAV-2i8, as well as variants of LK03 (SEQ ID NO:3), Spk100 (SEQ ID NO:4), AAV1, AAV2, AAV3, AAV4, AAV5, AAV6, AAV7, AAV8, AAV9, AAV10, AAV11, AAV12, Rh10, Rh74, AAV3B and AAV-2i8.

The invention provides kits with packaging material and one or more components therein. A kit typically includes a label or packaging insert including a description of the components or instructions for use in vitro, in vivo, or ex vivo, of the components therein. A kit can contain a collection of such components, e.g., a cell line of the invention and optionally a second component, such as a component that provides virus helper functions.

A kit refers to a physical structure housing one or more components of the kit. Packaging material can maintain sterility, stability and/or purity of components and can be made of material commonly used for such purposes (e.g., paper, corrugated fiber, glass, plastic, foil, ampules, vials, tubes, etc.).

Labels or inserts can include identifying information of one or more components therein, including a method of using the components in the kit, such as producing a packaging system or rAAV particles as set forth herein. Labels or inserts can include information identifying manufacturer, lot numbers, manufacture location and date, expiration dates. Labels or inserts can include information identifying manufacturer information, lot numbers, manufacturer location and date.

Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a bar-coded printed label, a disk, optical disk such as CD- or DVD-ROM/RAM, DVD, MP3, magnetic tape, or an electrical storage media such as RAM and ROM or hybrids of these such as magnetic/optical storage media, FLASH media or memory type cards.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All patents, patent applications, publications, and other references, GenBank citations and ATCC citations cited herein are incorporated by reference in their entirety. In case of conflict, the specification, including definitions, will control.

Various terms relating to the biological molecules of the invention are used hereinabove and also throughout the specification and claims.

All of the features disclosed herein may be combined in any combination. Each feature disclosed in the specification may be replaced by an alternative feature serving a same, equivalent, or similar purpose. Thus, unless expressly stated otherwise, disclosed features are an example of a genus of equivalent or similar features.

As used herein, the singular forms "a", "and," and "the" include plural referents unless the context clearly indicates otherwise. Thus, for example, reference to "a nucleic acid" includes a plurality of such nucleic acids, reference to "a vector" includes a plurality of such vectors, and reference to "a virus" or "particle" includes a plurality of such viruses/particles.

As used herein, all numerical values or numerical ranges include integers within such ranges and fractions of the values or the integers within ranges unless the context clearly indicates otherwise. Thus, to illustrate, reference to 80% or more identity, includes 81%, 82%, 83%, 84%, 85%, 86%, 87%, 88%, 89%, 90%, 91%, 92%, 93%, 94%, etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-850, includes ranges of 1-20, 1-30, 1-40, 1-50, 1-60, 10-30, 10-40, 10-50, 10-60, 10-70, 10-80, 20-40, 20-50, 20-60, 20-70, 20-80, 20-90, 50-75, 50-100, 50-150, 50-200, 50-250, 100-200, 100-250, 100-300, 100-350, 100-400, 100-500, 150-250, 150-300, 150-350, 150-400, 150-450, 150-500, etc.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

A number of embodiments of the invention have been described. Nevertheless, one skilled in the art, without departing from the spirit and scope of the invention, can make various changes and modifications of the invention to adapt it to various usages and conditions. Accordingly, the following examples are intended to illustrate but not limit the scope of the invention claimed in any way.

Example 1

This example describes certain embodiments and aspects of the invention.

HEK293 cells, are a convenient and exemplary platform for both adherent and suspension culture.

In the cell lines of the invention, Rep protein is not substantially expressed before introduction of adenovirus E2A or E4 proteins and/or VA RNA. Such adenovirus helper sequences for rAAV production can be provided by infection with an adenovirus infection, an adenovirus—AAV hybrid virus infection, or transfection with another vector, or transfection of a plasmid.

In this exemplary system, no plasmid transfection is required, meaning that rAAV particles can be produced plasmid free.

In certain aspects, a single E1/E3 deleted Ad-AAV hybrid vector transducing the cells that have AAV rep/cap genes triggers rAAV production.

A cell density as high as 20E6/mL can be achieved.

In this system, no drug (antibiotic) selection is required to maintain any of the AAV gene, heterologous nucleic acid or helper sequences.

Certain observations have been made with respect to the system:

increased rAAV yield;

reduced DNA impurities;

the ratio of empty AAV to full vectors may be controllable;

easy to scale up for large scale rAAV production;

applicable to any AAV serotype;

substantial cost savings compared to the transient transfection with 3 different plasmids;

provides a more robust rAAV production process;

reduced labor and material costs;

clean genetic background, as there is no need to introduce drug resistance/antibiotic markers to select positive packaging/producer clones;

clean genetic background provides for safer manufacture of rAAV vectors;

long-term viability of packaging cells allows them to be stored in a cell bank for use;

potentially reduces empty AAV particles produced and also reduces DNA impurities that are packaged in rAAV vectors.

Example 2

TABLE 1 rAAV titer of 8 exemplary highly productive HEK 293 clones, after transfection with 2 plasmids, the 1st plasmid providing helper virus functions (E2A, E4 and VA RNA) and the 2nd plasmid with the AAV genome (AAV ITR flanked FVIII encoding sequence).

| Clone ID | Titer (vg/mL) |
|---|---|
| Clone 43G10 | 2.0 E+10 |
| Clone 42G9 | 1.5 E+10 |
| Clone 6E10 | 4.2 E+10 |
| Clone 1D11 | 4.6 E+10 |
| Clone 40B9 | 5.4 E+10 |
| Clone 8C6 | 4.3 E+10 |
| Clone 25F9 | 6.5 E+10 |
| Clone 1F11 | 4.8 E+10 |
| Control - Triple plasmid transfection | 4.0 E+10 |

Exemplary spacer sequence (SEQ ID NO: 1)

GCGCAGCCGCCAAGCCGAATTCTGCAGATATCCATCACACTGGCGGCCGC

TCGACTAGAGCGGCCGCCACCGCGGTGGAGCTCCAGCTTTTGTTCCCTTT

AGTGAGGGTTAATTGCGCGCTTGGCGTAATCATGGTCATAGCTGTTTCCT

GTGTGAAATTGTTATCCGCTCACAATTCCACACAACATACGAGCCGGAAG

CATAAAGTGTAAAGCCTGGGGTGCCTAATGAGTGAGCTAACTCACATTAA

TTGCGTTGCGCTCACTGCCCGCTTTCCAGTCGGGAAACCTGTCGTGCCAG

CTGCATTAATGAATCGGCCAACGCGCGGGGAGAGGCGGTTTGCGTATTGG

GCGCTCTTCCGCTTCCTCGCTCACTGACTCGCTGCGCTCGGTCGTTCGGC

TGCGGCGAGCGGTATCAGCTCACTCAAAGGCGGTAATACGGTTATCCACA

GAATCAGGGGATAACGCAGGAAAGAACATGTGAGCAAAAGGCCAGCAAAA

GGCCAGGAACCGTAAAAAGGCTTTCTACGGGGTCTGACGCTCAGTGGAAC

TCCGTCGAGAGGTCTGCCTCGTGAAGAAGGTGTTGCTGACTCATACCAGG

CCTGAATCGCCCCATCATCCAGCCAGAAAGTGAGGGAGCCACGGTTGATG

AGAGCTTTGTTGTAGGTGGACCAGTTGGTGATTTTGAACTTTTGCTTTGC

CACGGAACGGTCTGCGTTGTCGGGAAGATGCGTGATCTGATCCTTCAACT

CAGCAAAAGTTCGATTTATTCAACAAAGCCACGTTGTGTCTCAAAATCTC

TGATGTTACATTGCACAAGATAAAAATATATCATCATGAACAATAAAACT

GTCTGCTTACATAAACAGTAATACAAGGGGTGTTTAATCAGAATTGGTTA

ATTGGTTGTAACACTGGCAGAGCATTACGCTGACTTGACGGGACGGCGGC

TTTGTTGAATAAATCGCATTCGCCATTCAGGCTGCGCAACTGTTGGGAAG

GGCGATCGGTGCGGGCCTCTTCGCTATTACGCCAGCTGGCGAAAGGGGGA

TGTGCTGCAAGGCGATTAAGTTGGGTAACGCCAGGGTTTTCCCAGTCACG

ACGTTGTAAAACGACGGCCAGTGCCAAGCTTGCATGCCTGCAGGTCTAAA

TCAAAAGAATAGCCCGAGATAGAGTTGAGTGTTGTTCCAGTTTGGAACAA

GACGAAAAACCGTCTATCAGGGCGATGGCCCACTACGTGAACCATCACCC

TAATCAAGTTTTTTGGGGTCGAGGTGCCGTAAAGCACTAAATCGGAACCC

TAAAGGGAGCCCCCGATTTAGAGCTTGACGGGGAAAGCCGGCGAACGTGG

CGAGAAAGGAAGGGAAGAAAGCGAAAGGAGCGGGCGCTAGGGCGCTGGCA

AGTGTAGCGGTCACGCTGCGCGTAACCACCACACCCGCCGCGCTTAATGC

GCCGCTACAGGGCGCGTCCCATTCGCCATTCAGGCTGCGCAACTGTTGGG

AAGGGCGATCGGTGCGGGCCTCTTCGCTATTACGCCAGCTGGCGAAAGGG

GGATGTGCTGCAAGGCGATTAAGTTGGGTAACGCCAGGGTTTTCCCAGTC

ACGACGTTGTAAAACGACGGCCAGTGAGCGCGCGTAATACGACTCACTAT

AGGGCGAATTGGGTACCGGGCCCCCCCTCGAGGTCGACGGTATCGGGGGA

GCTCGCAGGGTCTCCATTTTGAAGCGGGAGGTTTGAACGCGCAGCCGCC

AAV2 P5 promoter (SEQ ID NO: 2)

GAGGGGTGGAGTCGTGACGTGAATTACGTCATAGGGTTAGGGAGGTCCTG

TATTAGAGGTCACGTGAGTGTTTTGCGACATTTTGCGACACCATGTGGTC

ACGCTGGGTATTTAAGCCCGAGTGAGCACGCAGGGTCTCCATTTTGAAGC

GGGAGGTTTGAA

-continued

LK03 capsid protein (SEQ ID NO: 3)

MAADGYLPDWLEDNLSEGIREWWALQPGAPKPKANQQHQDNARGLVLPGY

KYLGPGNGLDKGEPVNAADAAALEHDKAYDQQLKAGDNPYLKYNHADAEF

QERLKEDTSFGGNLGRAVFQAKKRLLEPLGLVEEAAKTAPGKKRPVDQSP

QEPDSSSGVGKSGKQPARKRLNFGQTGDSESVPDPQPLGEPPAAPTSLGS

NTMASGGGAPMADNNEGADGVGNSSGNWHCDSQWLGDRVITTSTRTWALP

TYNNHLYKQISSQSGASNDNHYFGYSTPWGYFDFNRFHCHFSPRDWQRLI

NNNWGFRPKKLSFKLFNIQVKEVTQNDGTTTIANNLTSTVQVFTDSEYQL

PYVLGSAHQGCLPPFPADVFMVPQYGYLTLNNGSQAVGRSSFYCLEYFPS

QMLRTGNNFQFSYTFEDVPFHSSYAHSQSLDRLMNPLIDQYLYYLNRTQG

TTSGTTNQSRLLFSQAGPQSMSLQARNWLPGPCYRQQRLSKTANDNNNSN

FPWTAASKYHLNGRDSLVNPGPAMASHKDDEEKFFPMHGNLIFGKEGTTA

SNAELDNVMITDEEEIRTTNPVATEQYGTVANNLQSSNTAPTTRTVNDQG

ALPGMVWQDRDVYLQGPIWAKIPHTDGHFHPSPLMGGFGLKHPPPQIMIK

NTPVPANPPTTFSPAKFASFITQYSTGQVSVEIEWELQKENSKRWNPEIQ

YTSNYNKSVNVDFTVDTNGVYSEPRPIGTRYLTRPL

Spark100 capsid protein (SEQ ID NO: 4)

MAADGYLPDWLEDNLSEGIREWWDLKPGAPKPKANQQKQDNGRGLVLPGY

KYLGPFNGLDKGEPVNAADAAALEHDKAYDQQLQAGDNPYLRYNHADAEF

QERLQEDTSFGGNLGRAVFQAKKRVLEPLGLVESPVKTAPGKKRPVEPSP

QRSPDSSTGIGKKGQQPAKKRLNFGQTGDSESVPDPQPIGEPPAAPSGVG

PNTMAAGGGAPMADNNEGADGVGSSSGNWHCDSTWLGDRVITTSTRTWAL

PTYNNHLYKQISNGTSGGSTNDNTYFGYSTPWGYFDFNRFHCHFSPRDWQ

RLINNNWGFRPKRLNFKLFNIQVKEVTQNEGTKTIANNLTSTIQVFTDSE

YQLPYVLGSAHQGCLPPFPADVFMIPQYGYLTLNNGSQAVGRSSFYCLEY

FPSQMLRTGNNFEFSYNFEDVPFHSSYAHSQSLDRLMNPLIDQYLYYLSR

TQSTGGTAGTQQLLFSQAGPNNMSAQAKNWLPGPCYRQQRVSTTLSQNNN

SNFAWTGATKYHLNGRDSLVNPGVAMATHKDDEERFFPSSGVLMFGKQGA

GKDNVDYSSVMLTSEEEIKTTNPVATEQYGVVADNLQQQNAAPIVGAVNS

QGALPGMVWQNRDVYLQGPIWAKIPHTDGNFHPSPLMGGFGLKHPPPQIL

IKNTPVPADPPTTFNQAKLASFITQYSTGQVSVEIEWELQKENSKRWNPE

IQYTSNYYKSTNVDFAVNTEGTYSEPRPIGTRYLTRNL

What is claimed:

1. A mammalian cell line expressing adenovirus (Ad) E1A protein, comprising:

a) an integrated adeno-associated virus (AAV) rep gene operably linked to a promoter, wherein a nucleic acid spacer from about 1700 to about 1800 nucleotides is positioned between said rep gene and said promoter, and b) an integrated AAV cap gene, wherein said promoter drives expression of said rep gene only in the presence of helper virus function, and wherein said helper virus function is provided by a hybrid Ad-AAV virus comprising said helper function and a heterologous nucleic acid sequence.

2. The cell line of claim 1, wherein said cell line is passagable for at least about 5 passages, at least about 10 passages, at least about 15 passages, or at least about 20 passages while E1A protein is expressed in the cell line.

3. The cell line of claim 1, wherein said cell line is passagable for at least about 5 passages, at least about 10 passages, at least about 15 passages, or at least about 20 passages without substantial death of said cell line.

4. The cell line of claim 1, wherein Rep protein expression from said rep gene increases in the presence of helper virus function.

5. The cell line of claim 1, wherein said helper virus function comprises at least one of adenovirus (Ad) E2A protein, Ad E4 protein and Ad VA RNA.

6. The cell line of claim 1, wherein said promoter comprises a constitutively active promoter.

7. The cell line of claim 1, wherein said promoter comprises a non-inducible promoter.

8. The cell line of claim 1, wherein said rep gene and said cap gene are integrated in tandem into chromosomal nucleic acid of said cell line.

9. The cell line of claim 1, wherein said cap gene is operably linked to a promoter.

10. A mammalian, adeno-associated virus (AAV) packaging cell line, said cell line expressing adenovirus (Ad) E1A protein, wherein said cell line comprises an integrated AAV rep gene operably linked to an AAV p5 promoter, wherein a nucleic acid spacer of from about 1700 to about 1800 nucleotides is positioned between said rep gene and said p5 promoter, and an integrated AAV cap gene, wherein Rep protein is expressed from said rep gene only in the presence of helper virus function provided by a hybrid Ad-AAV virus comprising Ad E2A protein, Ad E4 protein and Ad VA RNA, and a heterologous nucleic acid sequence.

11. The cell line of claim 1, wherein said hybrid Ad-AAV virus comprises:

a. a polynucleotide sequence encoding Ad E2A protein, Ad E4 protein and Ad VA RNA; and b. a heterologous nucleic acid sequence.

12. The cell line of claim 1, wherein said rep and/or cap genes were introduced into said cell line by way of a virus, vector, or plasmid.

13. The cell line of claim 1, wherein said rep and/or cap genes were introduced into said cell line by way of a lentiviral vector.

14. The cell line packaging system of claim 1, wherein said hybrid Ad-AAV virus lacks genes encoding Ad E1A and/or E3 proteins.

15. The cell line of claim 1, wherein said cell line is not a HELA or A549 cell line.

16. The cell line of claim 1, wherein said cell line comprises human embryonic kidney (HEK) cells.

17. The cell line of claim 1, wherein said cell line does not express SV40 large T antigen.

18. The cell line of claim 1, wherein said cell line can be cultured at a cell density of at least about $1\times10^6$, at least about $5\times10^6$, at least about $1\times10^7$ or at least about $2\times10^7$ cells/mL.

19. The cell line of claim 1, wherein expression of said AAV cap is driven by an AAV p40 promoter.

20. The cell line of claim 1, wherein maintaining said E1A, rep and/or cap gene or protein expression in said cell line does not require expression of a selectable marker or selective pressure.

21. The cell line of claim 1, wherein the gene encoding said Ad E1A and/or said rep gene is not disrupted by an intron having transcription termination sequences flanked by lox P sites.

22. The cell line of claim 1, wherein expression of said rep gene is driven by an AAV p5 promoter positioned less than about 5,000 nucleotides 5' of said rep gene start codon.

23. The cell line of claim 1, wherein expression of said rep gene is driven by an AAV p5 promoter in which there is a spacer sequence located between the 3' end of the AAV p5 promoter and the 5' end of said rep gene start codon, wherein said spacer sequence has a length of from about 250 to about 5,000 nucleotides.

24. A method of producing rAAV vector particles, comprising: transfecting said cell line of claim 1 with one or more viruses, vectors or plasmids comprising: a) a rAAV vector genome, said rAAV vector genome comprising a heterologous nucleic acid sequence flanked at the 5' and/or 3' end by AAV ITRs, and b) helper virus functions, thereby producing transfected cells with an AAV vector genome comprising a heterologous nucleic acid sequence and helper virus functions; and culturing said transfected cells under conditions allowing production of said rAAV vector particles.

25. The method of claim 24, wherein said AAV vector genome of a) and said helper virus functions of b) are provided by a single virus, vector, or plasmid.

26. The method of claim 24, wherein said AAV vector genome of a) and said helper virus functions of b) are provided by two or more viruses, vectors or plasmids.

27. A method of producing rAAV vector particles, comprising transfecting the cell line of claim 1 with a virus, vector or plasmid comprising polynucleotides encoding Ad E2A, Ad E4 proteins and Ad VA RNA, thereby producing transfected cells, and culturing said transfected cells under conditions allowing production of said rAAV vector particles.

28. The method of claim 24, wherein said transfected cells produce rAAV vector particles at a yield of about $1\times10^{10}$ to about $5\times10^{12}$ vector genomes (vg)/mL or produce empty AAV particles at a yield of about $1\times10^{10}$ to about $5\times10^{12}$ particles/mL.

29. A method of producing the cell line of claim 1, comprising transfecting mammalian cells under conditions allowing introduction of said genes and expression of said genes and/or proteins as set forth in claim 1.

* * * * *